(12) United States Patent
Shah et al.

(10) Patent No.: US 7,790,103 B2
(45) Date of Patent: Sep. 7, 2010

(54) EXTENDED USE DIALYSIS SYSTEM

(75) Inventors: Dilip Shah, Buffalo Grove, IL (US); Douglas Reitz, Green Oaks, IL (US); Samuel Ding, Libertyville, IL (US); Meir Dahan, Lincolnwood, IL (US); Gino Cicchello, Vernon Hills, IL (US); John A. Biewer, Palm Harbor, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 307 days.

(21) Appl. No.: 11/773,588

(22) Filed: Jul. 5, 2007

(65) Prior Publication Data

US 2009/0012450 A1    Jan. 8, 2009

(51) Int. Cl.
   *A61L 2/00*   (2006.01)
   *A61L 2/18*   (2006.01)
   *A61L 9/00*   (2006.01)
   *A61L 2/20*   (2006.01)
   *B01J 7/00*   (2006.01)

(52) U.S. Cl. .............................. 422/28; 422/29; 422/33; 422/305

(58) Field of Classification Search .................. None
   See application file for complete search history.

(56) References Cited

U.S. PATENT DOCUMENTS

| 4,204,956 | A |   | 5/1980  | Flatow |
|-----------|---|---|---------|--------|
| 5,336,165 | A |   | 8/1994  | Twardowski |
| 5,585,003 | A |   | 12/1996 | Van Newenhizen |
| 5,641,456 | A | * | 6/1997  | Rosenauer ............ 422/29 |
| 6,051,188 | A |   | 4/2000  | Spickermann |
| 6,379,617 | B1 |  | 4/2002  | Spickermann |
| 6,454,871 | B1 |  | 9/2002  | Labib et al. |
| 6,800,248 | B1 |  | 10/2004 | Masuda et al. |
| 6,846,299 | B2 | * | 1/2005 | Masuda et al. ............ 604/29 |
| 6,869,538 | B2 |  | 3/2005  | Yu et al. |

(Continued)

FOREIGN PATENT DOCUMENTS

EP    1116491    7/2001

OTHER PUBLICATIONS

Innovative Deoxygenation of Ozonated Water; International Ozone Association World Congress 1999 Annual Conference; Deaborn, MI; Aug. 25, 1999, GDT Corporation, Phoenix, AZ. pp. 1-8.

(Continued)

*Primary Examiner*—Elizabeth L McKane
*Assistant Examiner*—Regina Yoo
(74) *Attorney, Agent, or Firm*—K&L Gates LLP

(57) ABSTRACT

A medical fluid machine, such as a dialysis machine, includes a pump that pumps a medical fluid and sterile water or other disinfecting liquid, such as ozonated water, for flushing and reconditioning the medical fluid machine. The machine may also include a heater that heats the medical fluid or disinfecting solution in order to kill bacteria and other microorganisms that may contaminate the machine after use. Disinfecting the machine, and a disposable kit used with the machine, may allow re-use of the disposable within a reasonable amount of time after completion of the disinfecting procedure. Dialysate treated with ultra-violet light or water with low concentrations of ozone also helps make the disposable kits suitable for reuse.

14 Claims, 16 Drawing Sheets

U.S. PATENT DOCUMENTS

| | | |
|---|---|---|
| 6,902,670 B2 | 6/2005 | Ho |
| 2002/0179518 A1 | 12/2002 | Ho |
| 2003/0042201 A1* | 3/2003 | Sizelove et al. ............. 210/639 |
| 2003/0165401 A1 | 9/2003 | Daintree et al. |
| 2004/0050789 A1* | 3/2004 | Ash .......................... 210/646 |
| 2004/0120850 A1 | 6/2004 | Kaiser |
| 2005/0163655 A1* | 7/2005 | Lin et al. ...................... 422/33 |
| 2005/0209563 A1 | 9/2005 | Hopping et al. |

OTHER PUBLICATIONS

Written Opinion of the International Searching Authority for International Applicaton No. PCT/US2008/068952 mailed on Jan. 19, 2009.

* cited by examiner

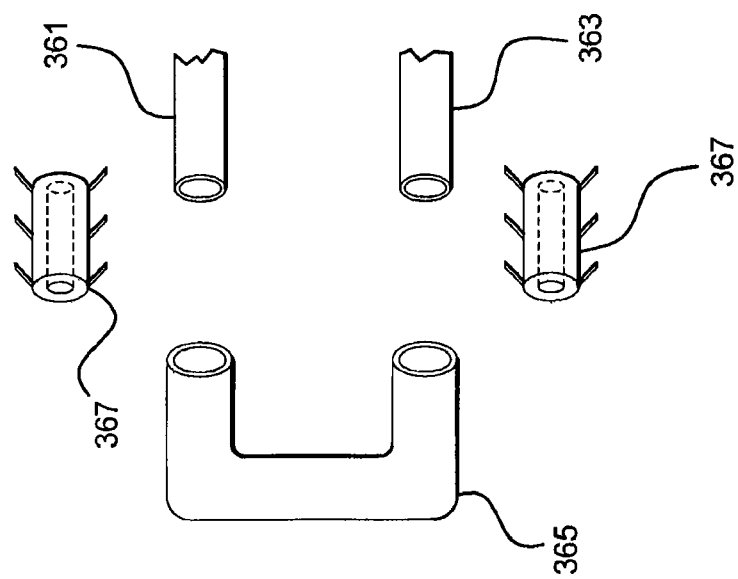
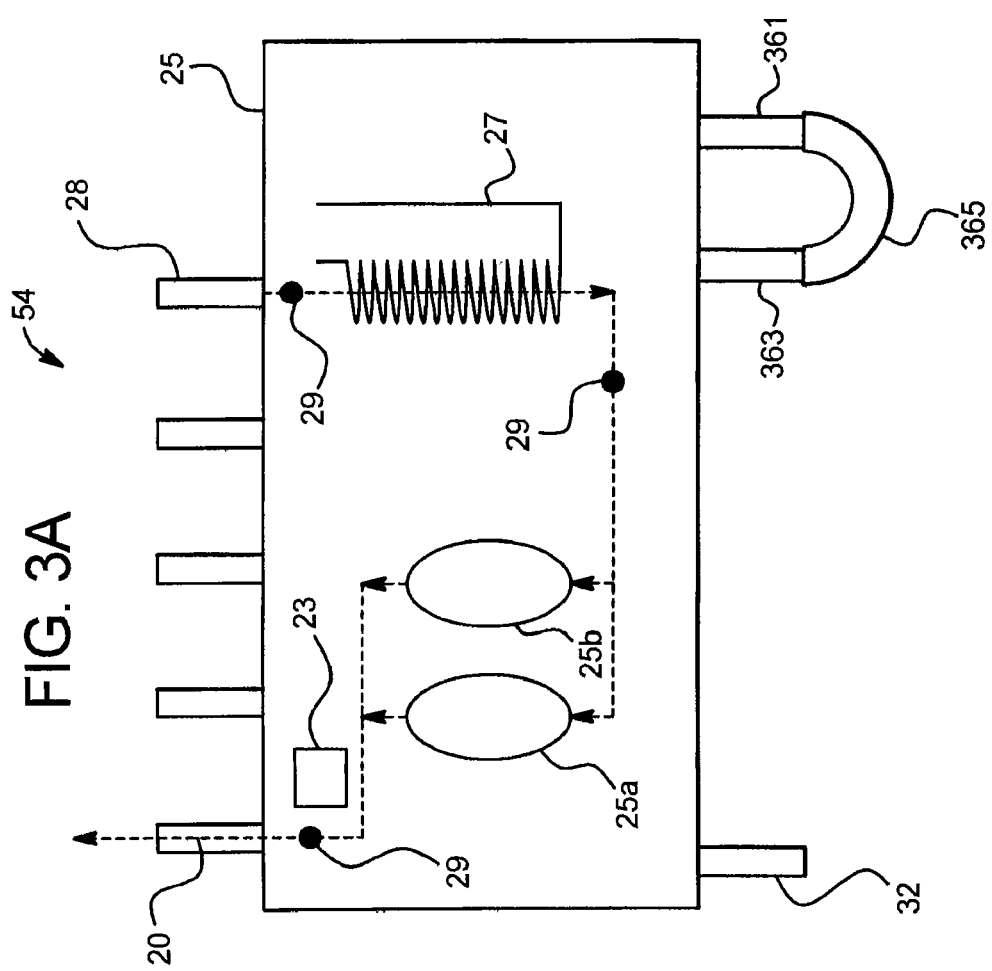

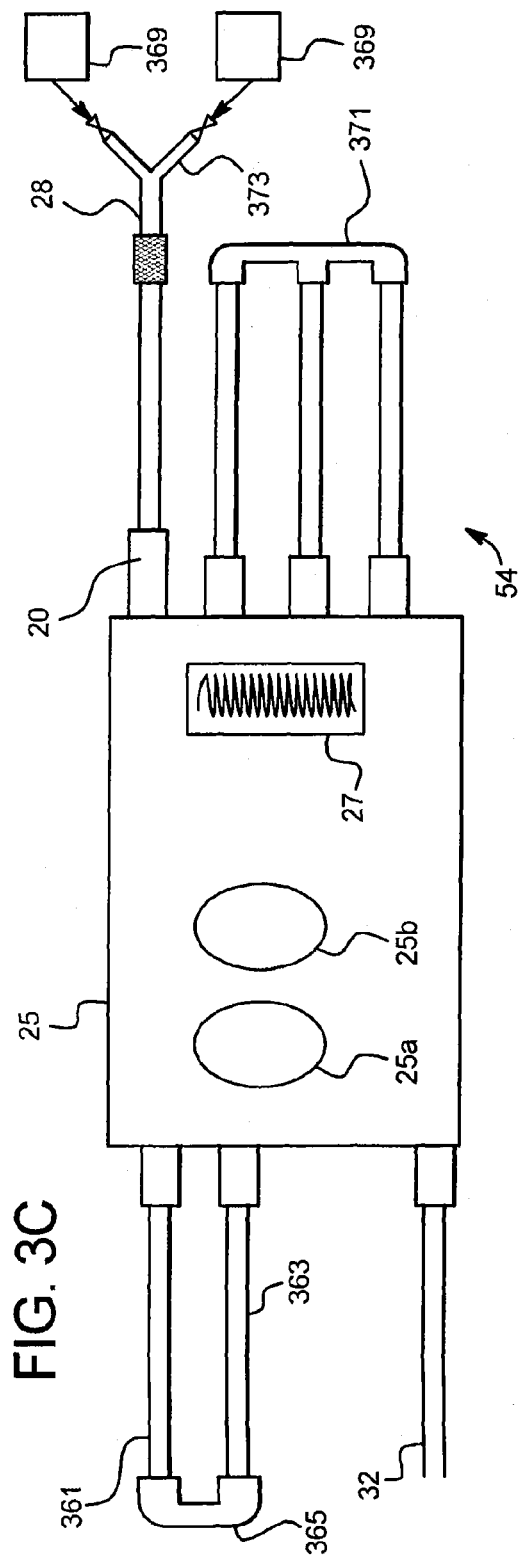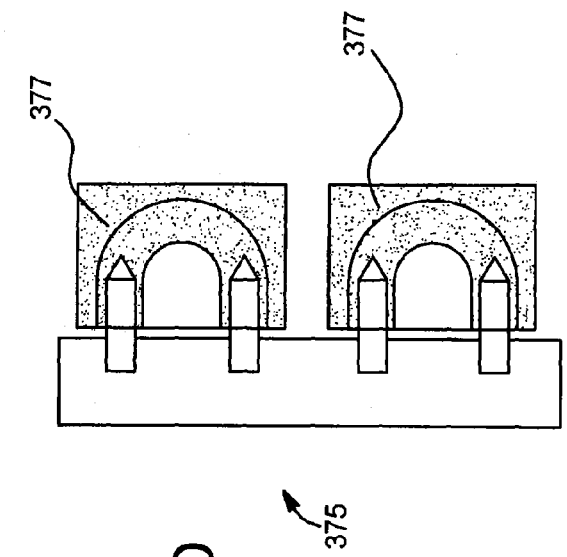

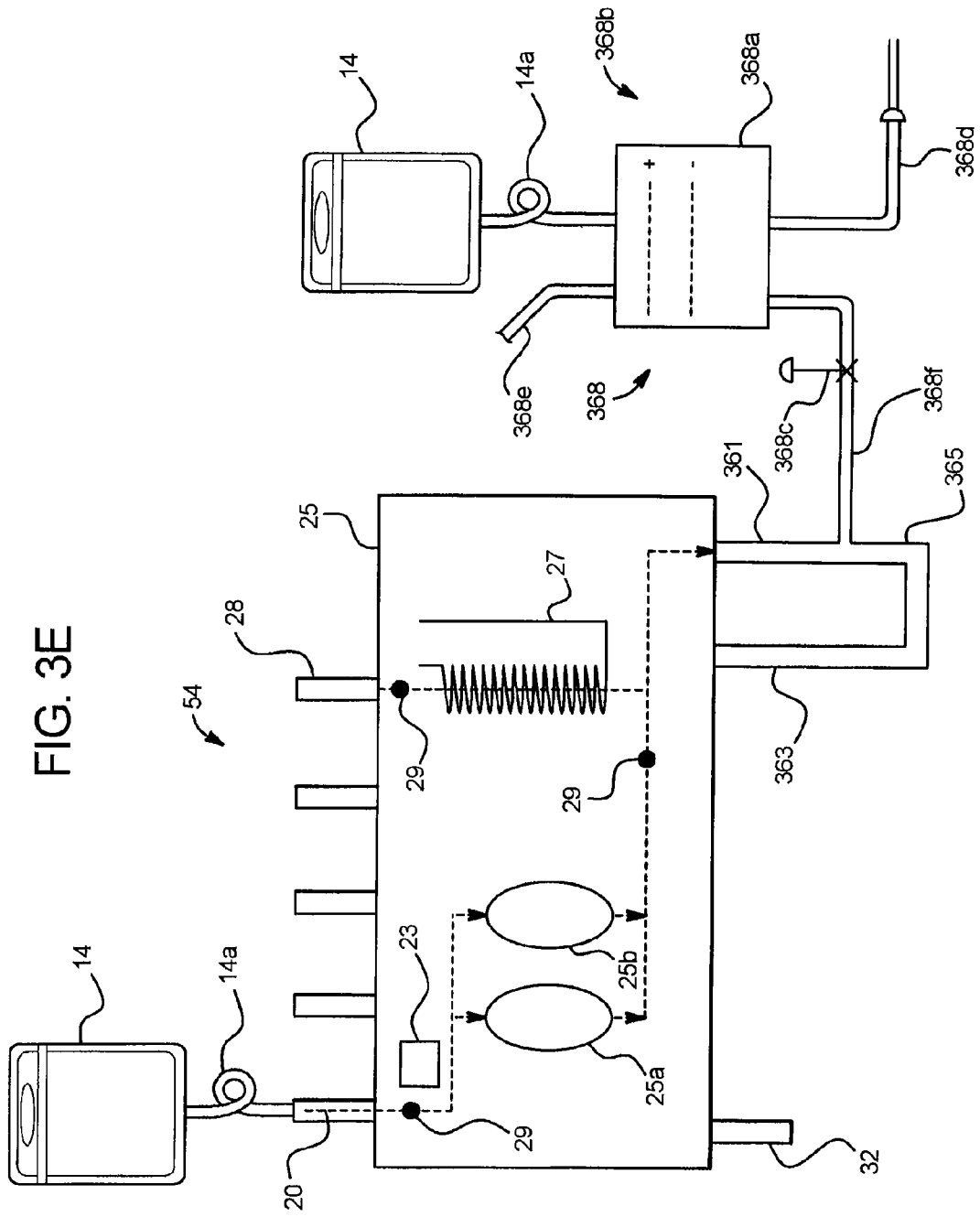

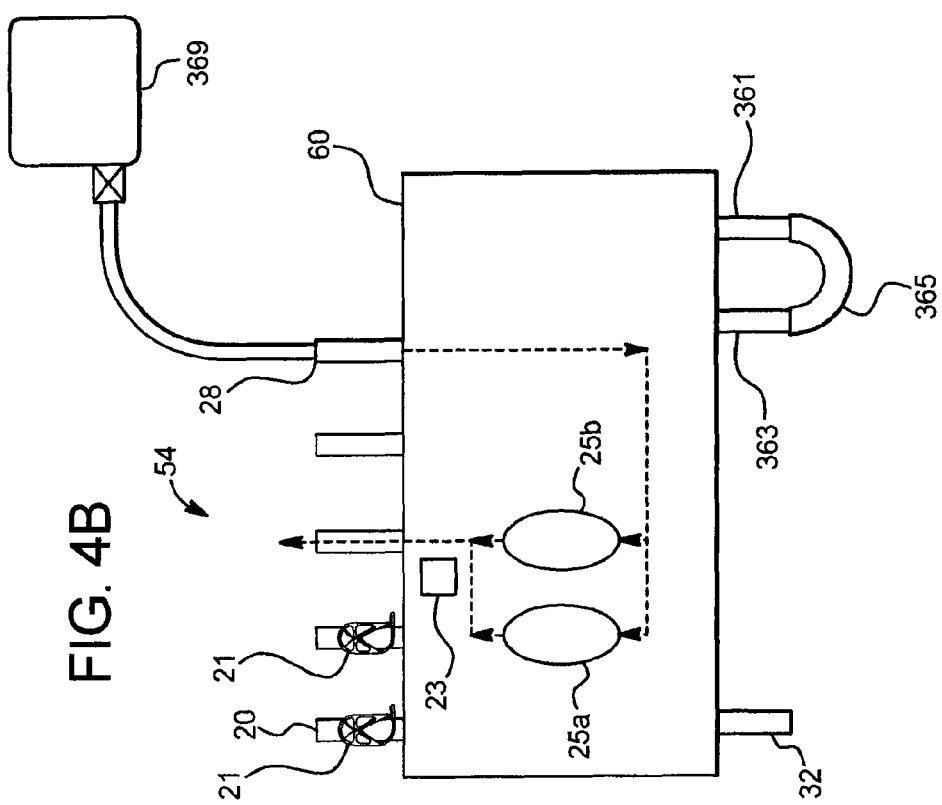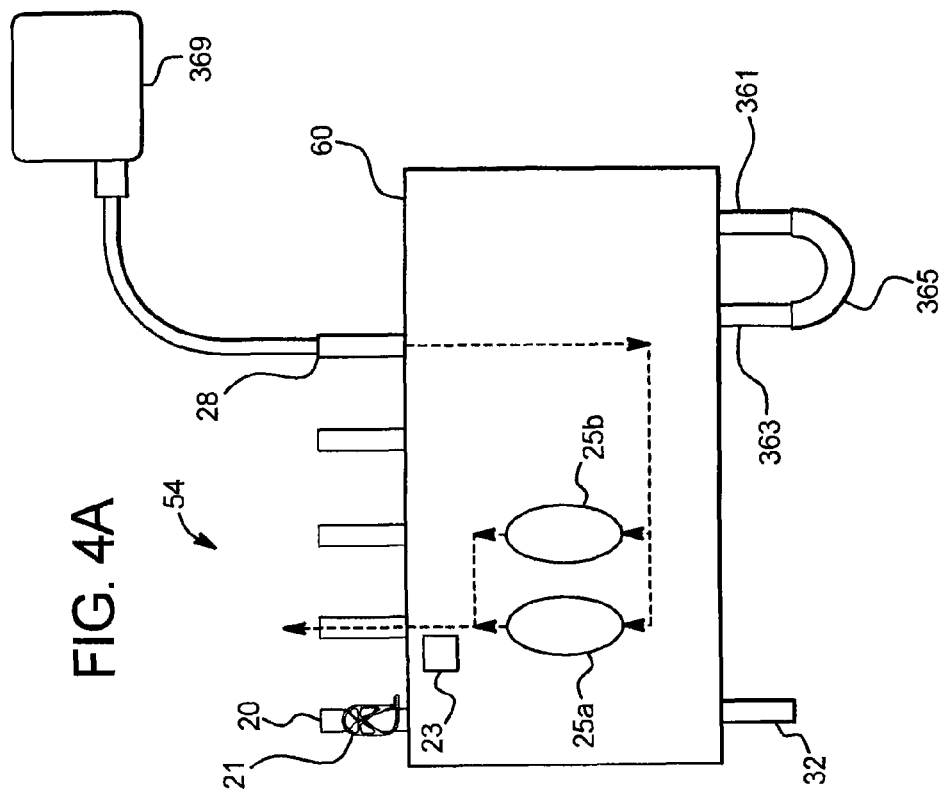

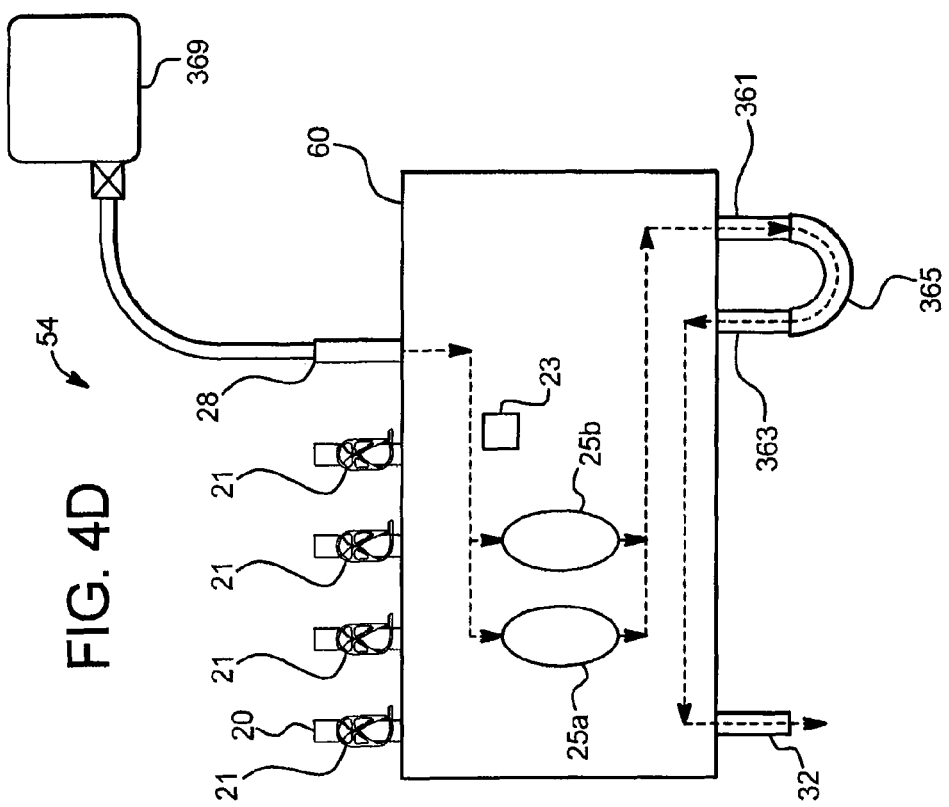
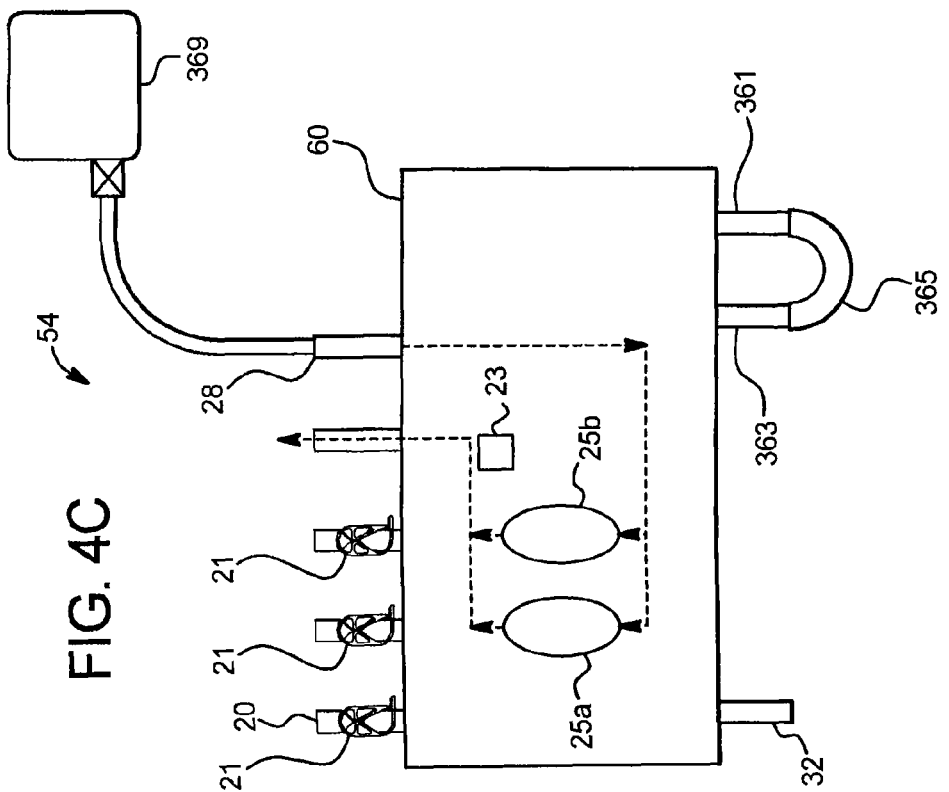

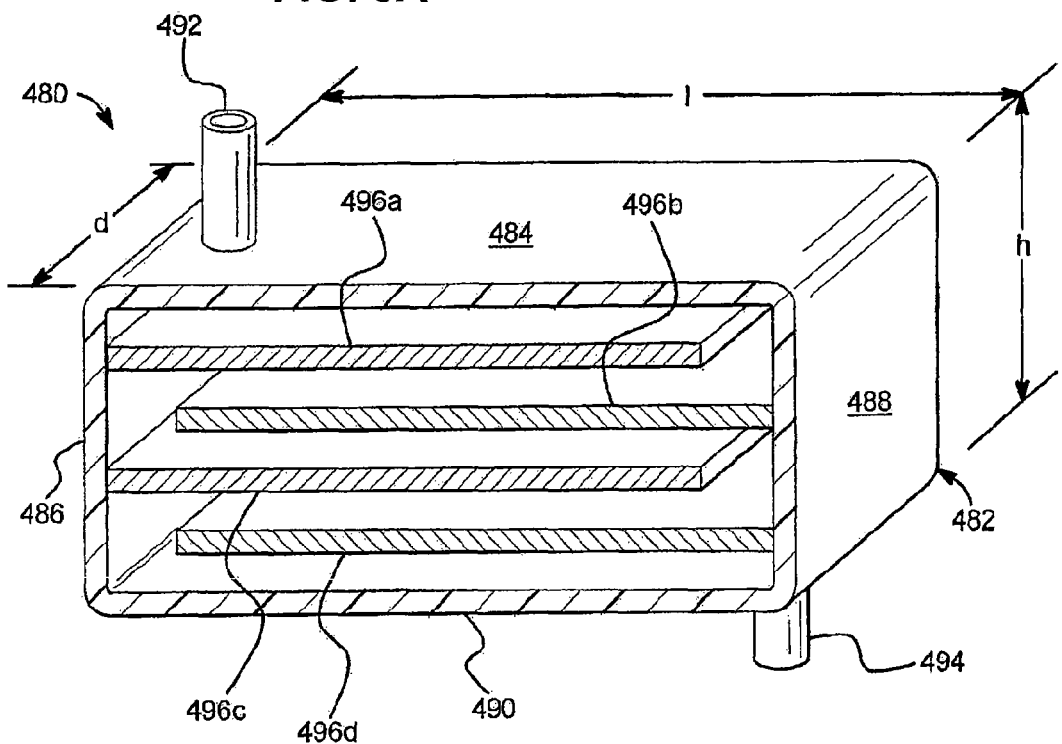
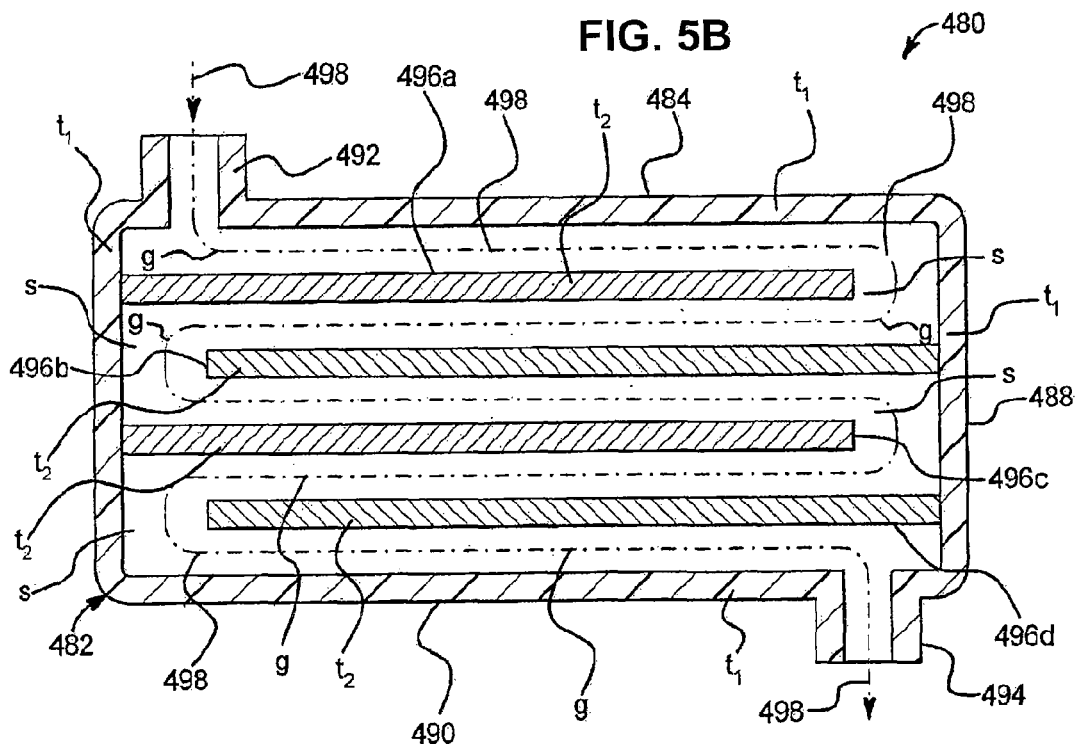

EXTENDED USE DIALYSIS SYSTEM

This patent is related to co-pending and co-owned U.S. patent application Ser. No. 11/675,470, filed Feb. 15, 2007, now U.S. Pat. No. 7,731,689, U.S. patent application Ser. No. 11/082,147, filed Mar. 16, 2005, now abandoned, and to U.S. patent application Ser. No. 10/155,560, filed May 24, 2002, now U.S. Pat. No. 6,869,538, all which are hereby incorporated by reference as though each page and figure were set forth fully herein.

BACKGROUND

In general, the present disclosure relates to medical fluid delivery systems that employ a disposable kit or cassette. In particular, the present disclosure provides systems and methods for cassette-based dialysis medical fluid therapies, including but not limited to those using peristaltic pumps and diaphragm pumps.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, or "dialysate," which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment. Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Hemodialysis, APD (including tidal flow) and CFPD systems can employ a pumping cassette. The pumping cassette typically includes a flexible membrane that is moved mechanically to push and pull dialysis fluid out of and into, respectively, the cassette. Certain known systems include flexible sheeting on one side of the cassette, while others include sheeting on both sides of the cassette. Positive and/or negative pressure can be used to operate the pumping cassettes.

One concern for dialysis systems is fluid or dialysate temperature heating. The dialysate needs to be heated to roughly body temperature or 37° C. before being delivered to the patient. For dialysate heating, it is desirable to have an apparatus that can be incorporated into, at least partially, and/or operate with a disposable dialysis kit or cassette. Another problem with dialysis systems is that the disposable kit is not re-used, even after only a short period of re-use. The kits cannot be reused because once they are used, and exposed to body fluids of a patient, they are viewed as incubators of the bacteria or other microorganisms from the patient. This problem is exacerbated by the need for heating and the higher temperatures which accelerate the growth of bacteria and other microorganisms.

The present disclosure addresses the above-described needs and concerns.

SUMMARY

One embodiment is a method for extending use of a disposable kit of a dialysis system. The method includes steps of providing a disposable kit for use in a dialysis system, providing dialysis for a patient, by circulating dialysis solution through the disposable kit from at least one supply line for dialysate solution to a patient output line and back from the patient through a recirculation line, at least one of the lines running through the disposable kit, and connecting the patient output line to the recirculation line. The method also includes steps of generating ozone to prepare a disinfecting solution, flushing the disinfecting solution through the patient output line and recirculation line, flushing the disinfecting solution through a pump and the at least one supply line for dialysate solution, draining the disinfecting solution from the disposable kit before a subsequent use of the disposable kit, and rinsing the disposable kit, including at least one supply line, the pump, the patient output line and the recirculation line with sterile water before a subsequent use of the disposable kit, wherein one of the steps of flushing includes vaporizing a portion of the disinfecting solution.

Another embodiment is a method for extending use of a cassette for a dialysis system. The method includes steps of providing a disposable kit for use in a dialysis system, connecting an output line of the kit to a recirculation line of the kit, generating ozone to prepare a disinfecting solution, and flushing the disinfecting solution through a supply line into the kit. The method also includes flushing the disinfecting solution through a pump, the output line, and the recirculation line, wherein the disinfecting solution is subjected to pressure cycles while being pumped, draining the disinfecting solution from the disposable kit before a subsequent use of the disposable kit, and rinsing the disposable kit, including the supply line, the pump, the output line and the recirculation line before a subsequent use of the disposable kit.

Another embodiment is a dialysis machine. The dialysis machine includes a housing, a controller, a heater in operable communication with the controller, an ozone generator controlled by the controller, and an interface for a disposable cassette, wherein the ozone generator is configured for generating an ozone concentration of at least about 0.5-5 ppm in sterile water, wherein the dialysis machine and the ozone generator are configured to kill microorganisms so that the cassette and a plurality of connecting lines may be reused.

Additional features and advantages of the present disclosure are described in, and will be apparent from, the following Detailed Description of the Disclosure and the figures.

BRIEF DESCRIPTION OF THE FIGURES

FIGS. 3A and 3C depict schematic views of different embodiments of reusable dialysate disposable cassettes, and FIGS. 3B and 3D depict additional equipment for use with alternate embodiments of dialysate disposable cassettes.

FIGS. 3E, 3F, and 3G depict ozonation embodiments of an extended use dialysis machine and cassette;

FIGS. 4A to 4D depict schematic views of plumbing embodiments for sterilizing a dialysate system.

FIGS. 5A and 5B are perspective and front elevation views, respectively, of one embodiment of an inductive disposable-cassette mountable dialysis fluid heater.

DETAILED DESCRIPTION

The present disclosure relates to medical fluid delivery systems that employ a pump, such as a diaphragm pump or a peristaltic pump. In particular, the present disclosure provides systems, methods and apparatuses for kit or cassette-based dialysis therapies including but not limited to hemodialysis, hemofiltration, hemodiafiltration, any type of continuous renal replacement therapy ("CRRT"), congestive heart failure treatment, CAPD, APD (including tidal modalities) and CFPD. The cassette or kit is disposable and typically discarded after a single use or therapy, reducing risks associated with contamination.

Patient Care

Figure 1A:
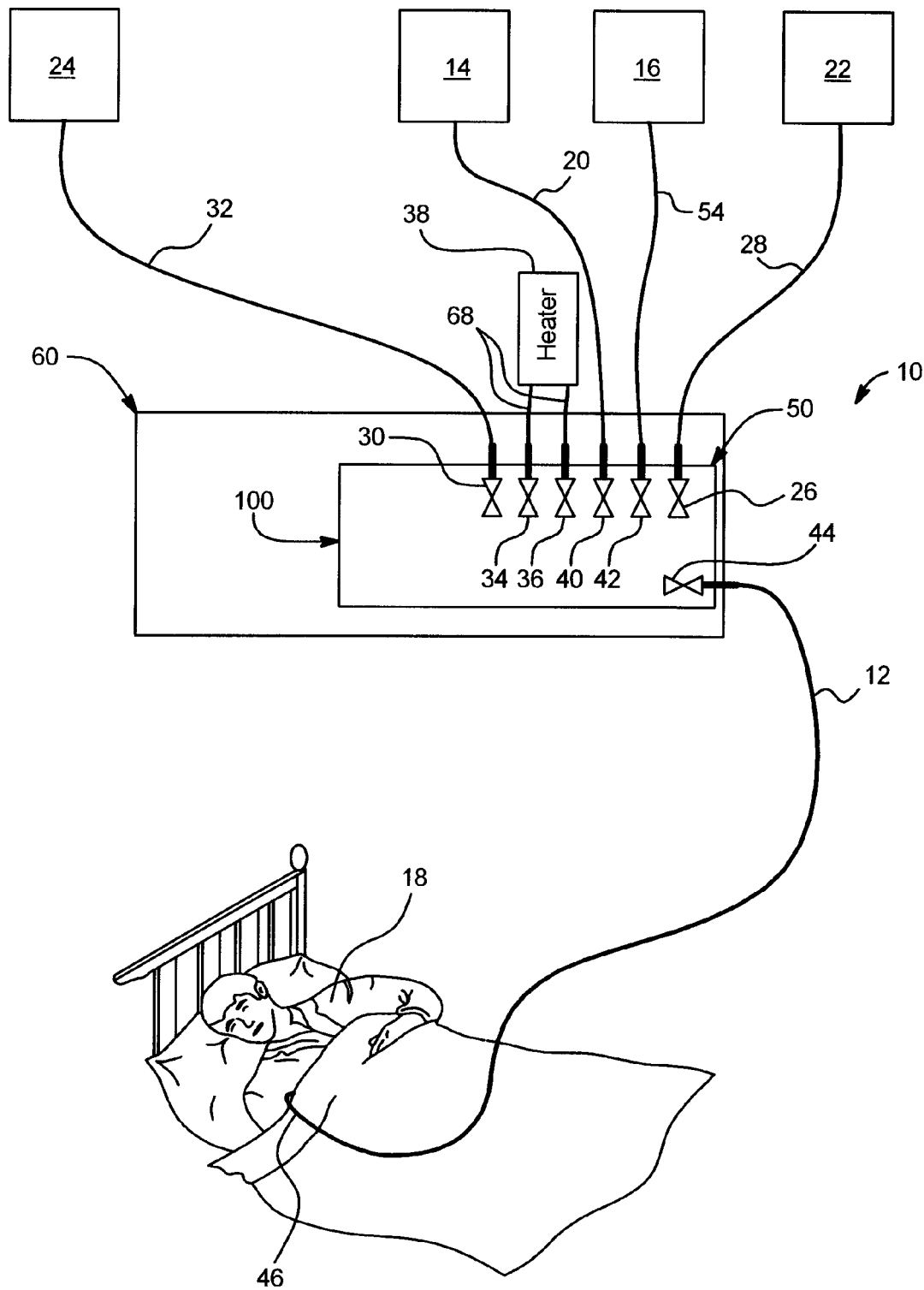
FIGS. 1A and 1B are perspective views of an overall patient therapy apparatus and method.

Referring now to the drawings and in particular to FIG. 1A, the teachings of the present invention, while applicable to each and all of the above-mentioned types of therapies, are described for ease of illustration by a peritoneal dialysis system 10. FIG. 1A shows system 10 in operation with a patient 18. Subsequent figures discuss the details of the primary components of system 10, namely, a disposable cassette and an instrument that operates with the cassette. As will become apparent, the peristaltic type of system illustrated is not critical to the teachings of the present invention in many cases and such teachings are readily applied to different types of medical fluid therapy systems known to those of skill in the art. As discussed in more detail below, system 10 includes a disposable cassette 50. Cassette 50 includes or defines fluid paths, valves chambers and a peristaltic pump tube and rollers. A dialysis machine or unit 60 operates the valves and pump to control the amount of fluid delivered to and removed from the patient 18.

A cassette-based system 10 controllably and selectively pumps exchange fluid volumes through lines 12, 20, 32, 28 and 54 between patient 18 and bags 14, 24, 22 and 16, respectively. Tube 12 is provided from cassette 50 to administer and remove exchange volumes of fluid, such as dialysate, to and from patient 18. Supply reservoir or bags 14, 16 and 22 contain supply dialysate volumes to be administered to patient 18. Bags 14, 16 and 22 can be of any suitable size, such as six liters each. Bags 14, 16 and 22 are connected fluidly to cassette 50 via lines 20, 54 and 28, respectively. A recovery reservoir 24 recovers used or spent dialysate from patient 18. A system controlled valve 26 is connected fluidly to line 28, which is connected to reservoir 22. A system controlled valve 30 is connected fluidly to line 32, which is connected to spent fluid reservoir 24. Valve 30 controls flow to spent reservoir 24 and prevents used dialysate from being released accidentally from recovery reservoir 24.

In the illustrated embodiment, cassette 50 of system 10 includes or defines seven valves 26, 30, 34, 36, 40, 42 and 44. Valves 26, 30, 40, 42 and 44 control fluid flow from bags 14, 16, 22 to patient 18 and back to bag 24 and one or more of bags 14, 16 and 22. Supply bags 14, 16 and 22 can double as drain or waste bags, cooperating with bag 24. Valves 34 and 36 control fluid flow to heater 38. Once heated dialysate fluid is delivered via line 12 to the peritoneal cavity of patient 18, waste and toxins are transferred across the patient's peritoneal membrane to the dialysate in a manner that is well known. The above-described fluid communication enables one or more fluid exchanges in the peritoneal cavity to take place. During a first volume exchange, pump 100 may remove an initial volume of liquid from patient 18 and pump that volume to the initially empty reservoir bag 24. In one embodiment, drain bag 24 is sized to receive all spent fluid from patient 18 (beginning from bags 14, 16 and 22), isolating fresh tubes from the spent fluid tube 32.

The direction of fluid flow is controlled by valves 26, 30, 40, 42 and 44, the tubing, the cassette pathways and pump 100. Pump 100 refers to the drive or instrument portion of the pump as well as the tubing and cassette portion 78 shown below. Pump 100 in one embodiment is driven in a single direction for both the pump-in and pump-out cycles of the therapy. In that case, valves 26, 30, 40, 42 and 44 switch to direct the flow of fluid from the correct source to the correct destination. Alternatively, pump 100 pumps in the opposite direction in cooperation with valves 26, 30, 40, 42 and 44 to pump spent dialysate from patient 18.

In either case, once inside the peritoneal cavity, waste and toxins are transferred to the exchange volume across the patient's peritoneal membrane in a manner that is well known. In either case, when delivering fluid to patient 18, the fluid, via valves 34 and 36 is pumped though inline heater 38. Inline heater 38 can be an electrical plate heater, an infrared heater, a convective heater, a radiant heater and any combination thereof. One control scheme for controlling heater 38 is described and claimed in U.S. Ser. No. 10/155,560, entitled Method and Apparatus for Controlling a Medical Fluid Heater, the entire contents of which is incorporated herein by reference. System 10 in one embodiment employs a pump 100 that can pump at a flowrate of zero to about five hundred milliliters/minute. Pump 100 can pump from each of the supply bags 14, 16 and 22 sequentially or, in the case of admixing, from two or more of bags 14, 16 and 22 simultaneously. The valves used to determine which supply bags are active are actuated selectively and automatically via mechanical, electrical, electromechanical or pneumatic actuators, which are housed in unit 60.

Product Configurations

Figure 1B:
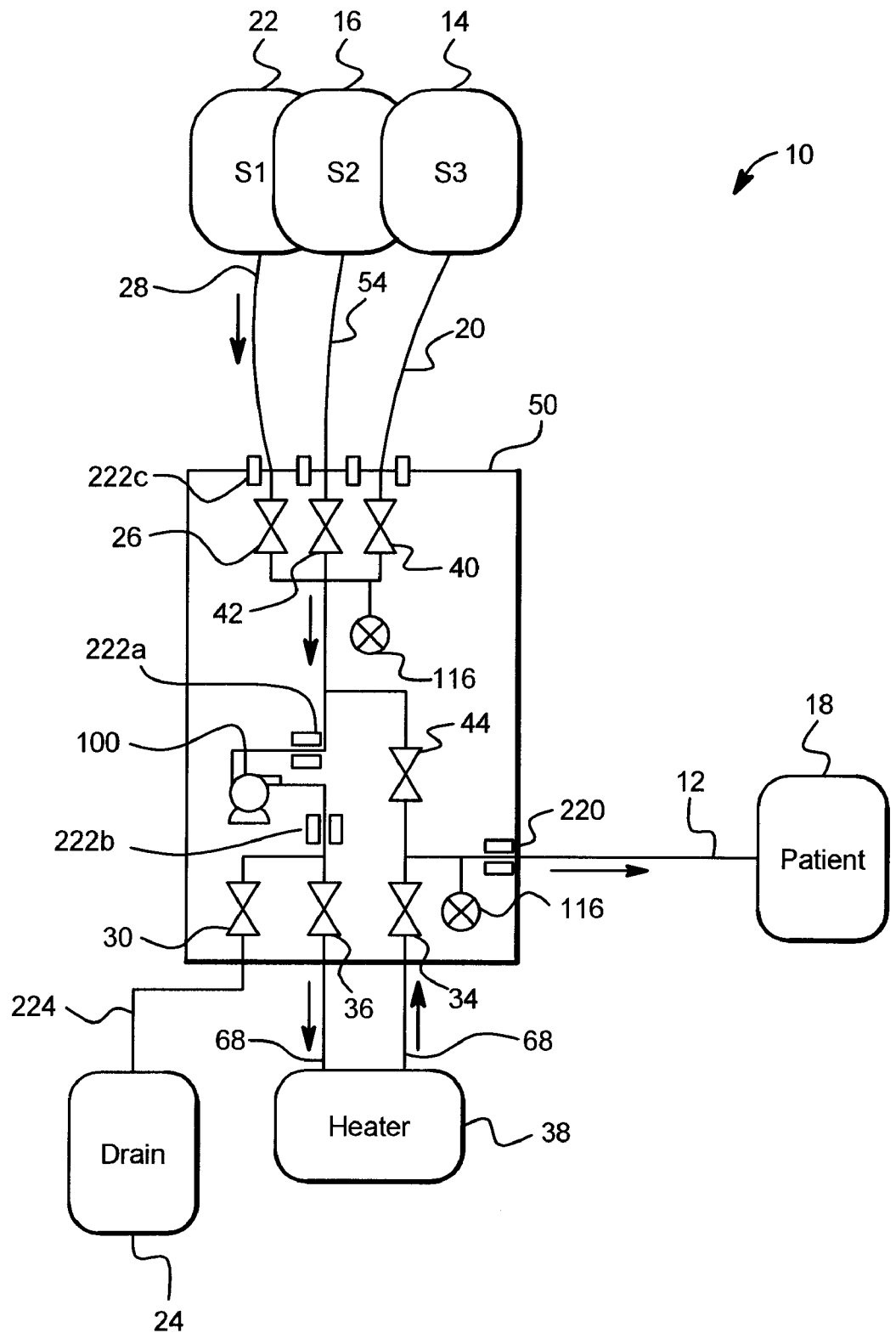

Referring now to FIG. 1B, one way for fluid to flow through the dialysis system is described. System 10 includes three dialysate supply bags 22, 16 and 14 that are coupled to inlet valves 26, 42, and 40, respectively, via supply fluid lines 28, 54 and 20. A pressure sensor 116 is positioned fluidly to sense the inlet pressure of the supply fluids. A second pressure sensor 116 is positioned to sense the outlet pressure of fluid delivered to the patient. The fluid supply flows past supply pressure sensor 116 and is pumped through pump 100. Pump 100 can pump either to drain 24 through valve 30 and drain line 224 or instead through heater 38 via valves 34 and 36 and heater lines 68. Valves 26, 42, 40, 34, 36, 30 and 44 operate with pump 100 to enable fluid to be sent to or pulled from patient 18. That is, if valves 44 and 30 are closed and valves 36, 34 and one of valves 26, 42 or 40 are open, pump 100 in a fill mode pumps fluid through heater 38 to patient 18. Alternatively, if valves 26, 42, 40, 36 and 34 are closed, isolating heater 38, and valves 44 and 30 are open, pump 100 pumps fluid from patient 18 to drain 24. In other embodiments, there may be separate lines connecting to and from the patient.

System 10 may also include air detection sensors 220, and 222a, 222b, 222c, at various junctures in the system to detect air that needs to be removed before therapy begins. Sensor 220 is positioned at the last possible juncture before delivery of fluid to the patient, while other sensors 222a, 222b, 222c are positioned for detection of air, and thus leaks, in the cassette well before the system as a whole is contaminated, giving users the opportunity to fix leaks and purge the system well before delivery to the patient is contemplated. Regarding sterile air that enters the system via the solution bags, that air is typically sensed towards the end of the current fill cycle when the supply bag has been largely emptied. At that time sterile air in the supply bags is prone to being pumped into cassette 50. System 10 provides air detection sensors for detecting such air and for removing it from the dialysate circuit before resuming therapy. For instance, fluid may be drained through valve 30 if contamination is detected.

Referring now to FIGS. 2A to 2D a first configuration for the components of system 10 is illustrated by configuration 350. As discussed herein, in one embodiment the pumping technology used for system 10 is a peristaltic pump. It is expressly contemplated, however, that many features and embodiments discusses herein can be used with peristaltic pumps, volumetric pumps, pumps operated pneumatically, pumps operated mechanically, pumps operated hydraulically and any combination thereof. The component features discussed in connection configuration 350 and indeed in connection with configurations 370 and 390 shown in connection with FIGS. 2A to 2D and 3A to 3F, respectfully, are applicable to any of the different types of pumping technologies just previously described. Indeed, while cassette 50 is shown in connection with each of configuration 350, 370 and 390.

Figure 2A:
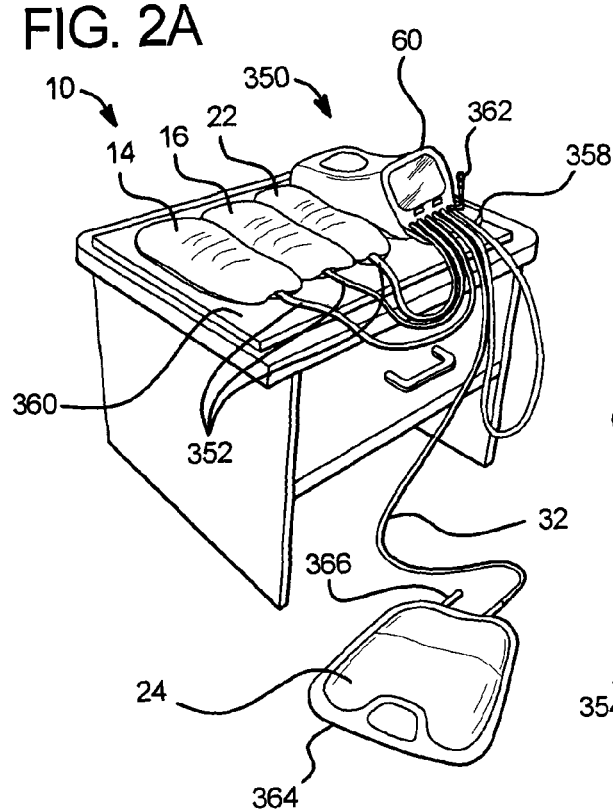
FIGS. 2A to 2D are perspective views illustrating different components of configurations of a dialysis system employing the embodiments discussed herein.

As seen in FIG. 2A, configuration 350 of system 10 includes supply bags, 14, 16, and 22 and drain bag 24. Those bags are connected fluidly to machine or unit 60 via lines 28, 54, 20 and 32, respectfully, as seen in FIG. 2C additionally. FIG. 2A further illustrates that configuration 350 can be placed partly on a desk or nightstand, with drain bag 24 being placed on the floor. In the illustrated embodiment, supply bags 14, 16 and 22 and cassette 50 are loaded and maintained in an at least substantially horizontal configuration.

Figure 2B:
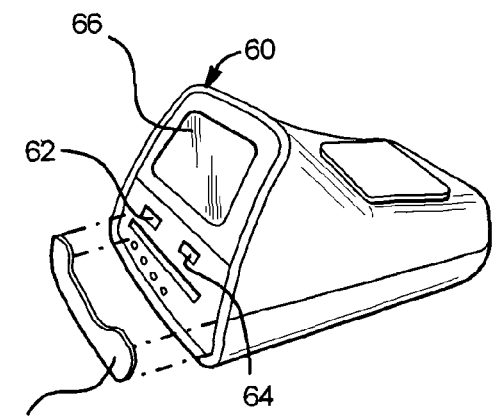
Figure 2C:
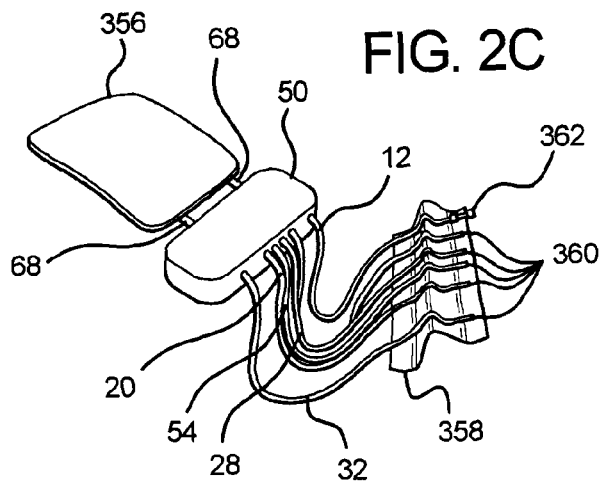

Referring now to FIG. 2B, dialysis machine or unit 60 is illustrated in more detail. Here, unit 60 is a single integrated device, which includes a horizontal front drawer 354, the back of which curves vertically, so that a portion of cassette 50 is turned vertically for air separation purposes. Cassette 50 and heater bag 356, shown in more detail in connection with FIG. 2C, are loaded via drawer 354 simultaneously into unit 60. Drawer 354 also aids in organizing cassette 50 and heater bag 356 to aid the patient in aligning, inserting and removing those items. To that end, the identification of the separate lines 28, 54, 20 and 32 is also shown on drawer 354, so that the patient can match corresponding indicia on the lines with the markings on drawer 354 for proper cassette installation. In the illustrated embodiment, display 66 of machine or unit 60 is tilted at an angle of about forty-five degrees to about sixty degrees from vertical for ready viewing. Other angles could also be used. Unit 60 also includes controls 62 and 64, which can be off-screen controls, such as membrane switches, or on-screen controls, such as a touch screen overlay.

Referring now to FIG. 2C, the disposable, sterile, fluid carrying portion of configuration 350 is illustrated. The disposable set includes cassette 50 and separate heater bag 356, which are connected together via heater tubes. Thus, in configuration 350, heater 38 is located inside machine 60. As discussed above, unit 60 cooperates with drawer 354 to turn a portion of heater bag 356 upwards for air separation. In the illustrated embodiment, heater bag 356 is loaded first via drawer 354 into unit 60. The distal or free end of heater bag 356 is turned upward. That end may contain a vent or a filter, such as a hydrophobic membrane, which enables air escaping from the fluid in the heating pathway to collect at the vertical upper end of heater bag 356 and to eventually be vented through such a vent or filter.

The disposable set includes a tubing organizer 358, which can be placed on the table or night stand to further assist the loading of cassette 50 and heater bag 356. Organizer 358 holds supply lines 28, 54 and 20 next to one another. Those lines in an embodiment are tacked or otherwise held together, so that the patient knows that those lines are intended to be connected to supply bags 22, 16 and 14, respectively. Drain line 32 in an embodiment has a larger diameter hose than do supply lines 28, 54 and 20. This also helps the patient to keep the different lines straight in the patient's memory. Thus it should be appreciated that in configuration 350, cassette 50 and the lines connected to organizer 358 are loaded through the front of the unit 60, which places the tubes in an advantageous viewing area in front of the patient.

Figure 2D:
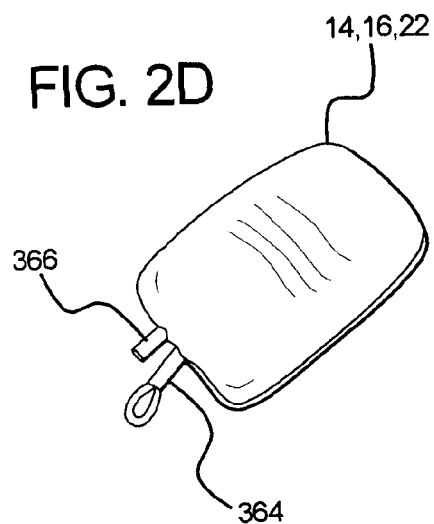

The identification of supply lines 28, 54 and 20, drain line 32 and patient line 12 is further aided via identifying markings. For example, clamps 360 (FIG. 2C) located at the distal ends of supply lines 20, 54, and 28 and drain line 32 are color-coded. The clamps may include line identification or indicia, molded into the clamps or placed or printed nearby. Patient line 12 is identified via a connector 362 at its distal end. Connector 362 is removeably fixed to unit 60 as seen in FIG. 2A for priming. Unit 60 in one embodiment has a sensor, which senses whether connector 362 of patient line 12 is in proper position for priming before allowing therapy to begin and that the patient line has been properly primed before allowing therapy to begin. In some embodiments, if the sensor is not satisfied, the controller may prompt the patient to connect make the connection. As seen in FIG. 2D, supply bags 14, 16 and 22 each include a port 364 and a medication port 366. Ports 364 each include a seal, which is spiked via the ends of supply lines 28, 54 and 20. The seal eliminates the need for a clamp on supply bag port 364.

Disinfecting with Disinfecting Solution and Heating

As discussed above, it is desirable for the peritoneal dialysis systems described herein to be able to flow disinfecting solution, such as sterile water through the kit, and also to disinfect the kit by flowing and heating the disinfecting solution or sterile water. FIGS. 3A-3B depict schematic views of a dialysis machine and cassette 25 intended for re-use and an endcap which may be used for funneling sterilized water or other disinfecting solution within the cassette. Cassette 25 includes a plurality of input and output lines 54, as discussed above. Included are a first supply line 20 for connecting to a first source of dialysate fluid, a sterile water line 28 for connecting to a source of disinfecting solution or sterile water, and a drain line 32, for draining dialysate fluid from the system. The cassette includes a pump 23 for pumping fluid from a source of fluid using two pneumatic pumping chambers 25a, 25b. Other dialysis machines may use other pumps, such as peristaltic pumps, piston pumps, volumetric pumps, or any other suitable pumps.

Cassette 25 includes in-line heater 27 for heating fluid within the dialysis machine for disinfecting the machine and its lines. Temperature sensors 29 may be incorporated in one or more places to control the temperature of the sterilizing water and to insure that the lines of the machine are thoroughly heated to kill bacteria or other microorganisms remaining. Temperature sensors may include thermocouples, thermistors, or other suitable devices for detecting temperatures and reporting temperatures to the controller of the dialysis machine.

The system also includes an output line 361 for pumping dialysate fluid to the patient, and a recirculation line 363 for receiving dialysate fluid from the patient and recycling it. The patient output line 361 and patient input or recirculation line 363 is capped with an end cap 365. End cap 365 caps both lines and connects them fluidly, so that fluid flowing from line 361 flows directly into end cap 365 and then into recirculation line 363, without going through the patient. As seen in FIG. 3B, end cap 365 may simply be a C-shaped cap that connects lines 361, 363. Connectors, such as barbed connectors 367 may be used to simplify the connections. In some embodiments, no special end cap or connector is needed to connect the patient output line to the drain line, because the lines already include, respectively, male and female mating connectors.

Other embodiments are shown in FIGS. 3C and 3D. In the FIG. 3C embodiment, cassette 25 includes pumping chambers 25a, 25b, heater 27, first inlet 20, a disinfecting solution supply line 28 and two bags of disinfecting solution 369, such as sterile water, connected via a Y-tube 373. The remaining supply lines 54 may be capped by interconnecting end cap 371. As discussed above, the valves within a dialysis machine may be manipulated to allow the disinfecting solution to flow as desired, such as first to the heater and then to the remaining flow portions of the machine. In the embodiment of FIG. 3D of a portion of a cassette, two separate recirculation end caps 377, may be used. The end caps may be used, for example, to cap the ports and recirculate disinfecting solution if there is another circulation manifold 375 for connection to the disposable cassette. Such a wetted manifold may be part of a device for automatically connecting tubing from dialysate bags to a disposable cassette.

FIGS. 4A-4D depict configurations of another embodiment of a dialysis machine, machine 60 in which sterile fluid is used to sterilize the cassette and related lines so that they may be re-used. Dialysis machine 60 in FIGS. 4A-4D differs from dialysis machine 25 in FIGS. 3A-3D in that dialysis machine 25 includes an inline heater, discussed below, while dialysis machine 60 does not have an inline heater and may not have temperature sensors as described above. In FIG. 4A, patient output line 361 is capped via end cap 365 to patient input line 363 to prevent inadvertent spills. A source of disinfecting solution, such as sterile water bag 369 is connected to disinfecting solution input line 28. Disinfecting solution is pumped through disinfecting solution line 28, through water or dialysate lines connecting pumping chambers 25a, 25b and pump 23, and out through one or more of the input lines 54, preferably one at a time. In this example, input line 20 is closed or clamped off with clamp 21. In FIG. 4B, the process is repeated as before, but this time with lines two supply lines closed or clamped off with clamps 21. The process is repeated for each supply line that requires disinfection, which may be all supply lines, depending on how the input lines are arranged in a manifold. In FIG. 4C, the process is completed for the final supply line, supply line 4, with the three other lines 20, 54 clamped off with clamps 21. Finally, as seen in FIG. 4D, the disinfecting solution input line 28 is connected to the patient lines 361, 363, and sterile water is pumped through these lines to drain line 32.

This completes the disinfecting procedure for the kit and allows one to re-use the kit within a reasonable amount of time, as set by the manufacturer of the kit, the fluids being pumped through the kit, and the effectiveness of the disinfecting procedure. For example, regulations by the Food and Drug Administration (FDA) of the U.S. government may limit use of home dialysis solutions to a 48 hour time period. Reuse of the kit is preferably limited to a single reuse with strict attention being paid to the thoroughness of the disinfecting procedure, i.e., making sure that all lines are flushed and drained in a thorough manner, without leaving any fluid behind for contamination or for dilution of the dialysate solution when dialysis is resumed.

The disinfecting procedure may be enhanced by using heated solution or water, especially sterile water heated in-line. Any number of heaters may be used, such as resistance or induction heating. Heating of water in dialysis machine is disclosed in related and co-owned patent application Ser. No. 11/675,470, filed on Feb. 15, 2007, now U.S. Pat. No. 7,731,689, the contents of which are hereby incorporated by reference, as though each page of text and each sheet of drawings were physically set forth herein.

Extending Use by Killing Microorganisms with Ultraviolet Light and Ozone

It is well known that microorganisms may be killed by the use of ultraviolet light and by exposing the microorganisms to ozone. Ultraviolet light for these applications is typically UV-C, with a wavelength from about 180-290 nm. Lamps with a wavelength of about 185 nm (ozone producing) or about 254 nm are preferred. Without being bound to any particular theory, it is believed that UV light penetrates the outer cell walls of the microorganisms, where it passes through the cell body, reaches the DNA and alters the genetic material. Ozone produced by other methods, such as electrolytic separation of water, is also a source of ozone. Ozone is also cidal to microorganisms, but acts in a more chemical way to destroy microorganisms in water when the ozone is present in concentrations at least from about 0.3 to 0.6 mg/l (about 0.3 to 0.6 ppm by weight). Without being bound to any particular theory, it is believed that ozone decomposes into molecular oxygen and free-radical oxygen; the free radical oxygen then forms hydrogen peroxide with available water or reacts directly with microorganisms to destroy them.

FIG. 3E depicts a dialysis treatment instrument with a container of dialysis fluid 14, supply tubing, preferably with a pigtail 14a to prevent backflow, a disposable cassette 25 and an electrolytic ozone cell 368. The ozone cell 368 includes a housing 368a, an electrolytic cell 368b, an outlet valve 368c, and connections 368d to a power supply and 368e to a dialysis machine and controller. In this embodiment, the ozonated water passing through valve 368c and tubing line 368f flows to the patient output line 361, end-cap 365, and patient return line 363. Ozone cell 368 may be a part of cassette 25, but is preferably a part of a dialysis machine, such as dialysis machine 60. Such organisms include *Serratia marcescens* and *S. aureus*. One proton exchange membrane that has worked well in ozone generation is a perfluorinated proton exchange membrane sold by DuPont under the name Nafion™. Other ways to generate ozone from water include an electrolysis cell with a catalyst to speed up the reaction, such as titanium or platinum. As noted, the theoretical voltages used are relatively low, e.g., about 1.25 to 1.51 volts, while actual cell voltages used are about 2.5 to about 4.5 volts. Ozone generators may be purchased from a number of companies, including Azco Industries, Ltd., Surrey, B.C., Canada.

Ozone has the potential for allowing extended use because with ozone it is possible to kill microorganisms throughout the tubing and disposable cassette areas, in cassettes used for peritoneal dialysis and for hemodialysis. In general terms, the patient should follow the following procedure for ozone use. After a dialysis treatment, the patient should disconnect from the dialysis machine and aseptically cap off the patient input/output lines, and should also disconnect all dialysate supply bags and discard them. At least one sterile water bag should be placed or replenished on a sterile water supply line to the ozone generator, and the ozone generator output line is connected to an input of the disposable cassette, such as a heater input line. The supply ports and the patient tubing ends on the cassette are capped, as with end caps, such that all input supply lines and the patient line receive the circulating ozone solution, also known as the disinfecting solution. Note that it may be possible to disinfect a disposable, and the associated tubing, lines, connections, and so forth, without recirculation. That is, water with a high ozone concentration is very cidal to harmful microorganisms, and one may be able to completely clean the items with a few flushes, or conceivably a single flush. It is clearly better practice to circulate the disinfecting solution for at least 10-15 minutes, but simply flushing may be sufficient.

The patient presses a GO button on the dialysis machine control console to begin ozone circulation for a given time. After the given time, the ozone generator is turned off and sterile water is circulated for another 5-10 minutes. The water may then be drained to remove all traces of ozone and the previously-circulated ozonated water. However, it is preferable to leave the ozone-containing water in place, continuing the protection afforded by the ozone during the interim period before the next dialysis. When it is time for the next dialysis treatment, the ozonated water is flushed and replaced with fresh sterile water before circulating with fresh dialysate, or the ozonated water can be flushed directly with fresh dialysate. Ozone treatment may also be used before a first or a subsequent dialysis, to eliminate infection from an inadvertent touch-contamination.

It is believed also that pure water, such as deionized water (DI water), preferably with a conductivity of less than 50 microSiemens, is suitable for producing ozone-containing water. Other pure water, such as that produced by distillation or reverse osmosis, may be used. Lower conductivity water generally has lower organic and inorganic contaminants, which reduces the number and amount of by-products generated when they are oxidized with ozone. Preferably, water conductivity of about 1 to 10 microSiemens with no organic contaminants is favorable for producing an ozone-containing disinfecting solution. Cooler water, such as water from about 5 C to about 20° C., and even closer to freezing, is preferable for achieving a higher concentration of dissolved ozone in the disinfecting solution. At atmospheric pressure, ozone solubility is about 30 ppm at 5° C., and about 10 ppm at 27° C. This shows the importance of using water at a lower temperature while generating ozonated water. The higher solubility of ozone at lower temperatures helps in maintaining the ozone concentration for a longer time. Heating the ozone solution later releases some of the dissolved ozone for gas phase disinfection in hard-to-reach areas of the cassette and the associated tubing, connections, and so forth.

Figure 3F:
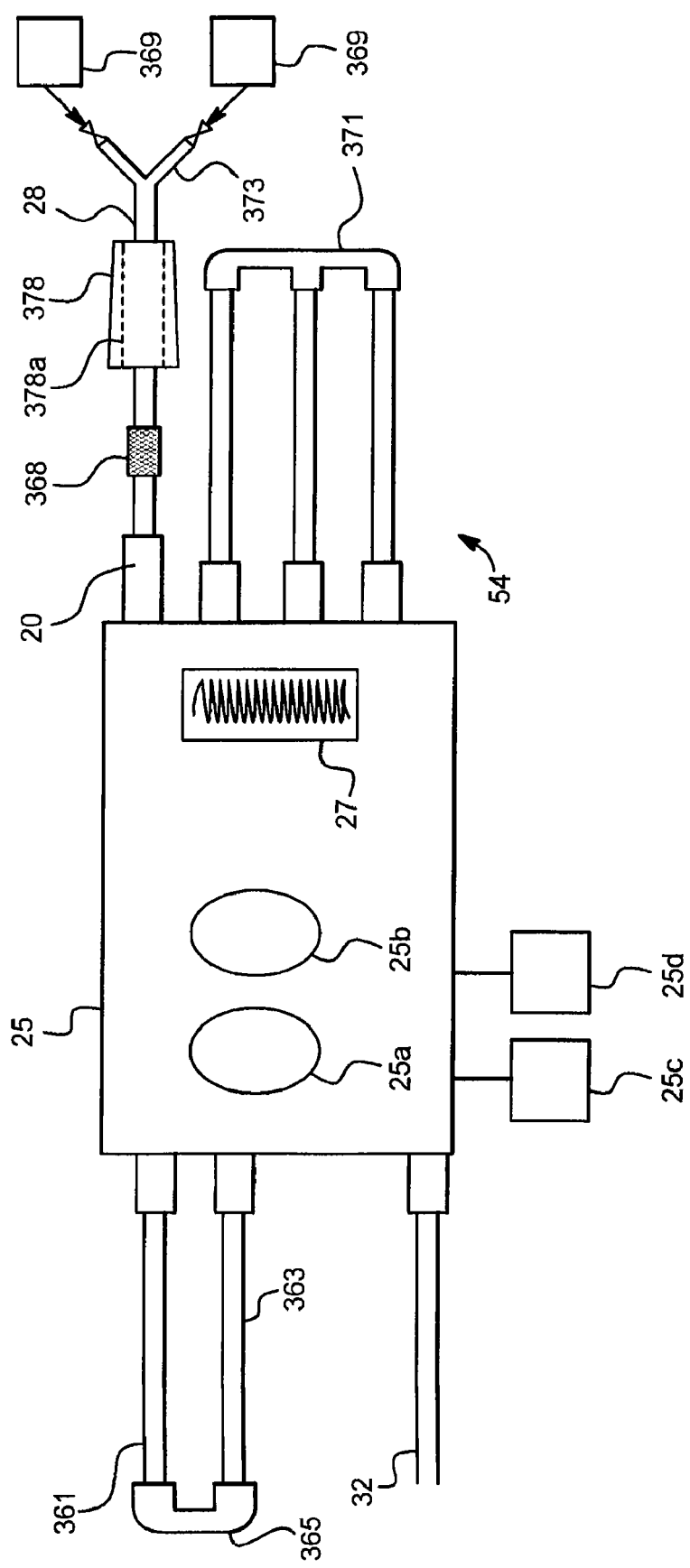

FIG. 3F depicts a disposable cassette 25 with an ozone-producing chamber 368. Ozone chamber 368 is connected to an input line 20 and to sources of sterile water 369 via a Y-connector 373. Ozone chamber 368 is preferably a part of a dialysis machine, whether a peritoneal dialysis machine or a hemodialysis machine, because the ozone chamber is relatively expensive and may be reused many times to treat and disinfect a dialysis disposable cassette. Sterile water 369 or other disinfecting fluid is then input to the ozone chamber 368 after passing through a temperature control chamber 378, which includes cooling coils 378a. Once the fluid has entered the ozone chamber, it is subjected to mild electrolysis in which a small amount of water in the fluid is reacted to form ozone ($O_3$) at the anode and hydrogen gas at the cathode. Hydrogen gas, like the ozone, is produced in very small amounts, and since it is produced at a separate electrode, it is easily separated and vented. The ozone enters the water and then engages in mild oxidation of trace organics, such as microorganisms. As noted above, water may be heated to help clean and disinfect the dialysis components. In the embodiment of FIG. 3F, the temperature control chamber 378 can cool water or other liquid close to 0° C., e.g., from 0 to 20° C., so that the water is more easily ozonated. Alternatively, a heat exchanger or cold plate may simply be added in-line, at a convenient location along the tubing lines. As noted above, cold water can hold a higher concentration of dissolved oxygen and ozone.

Figure 3G:
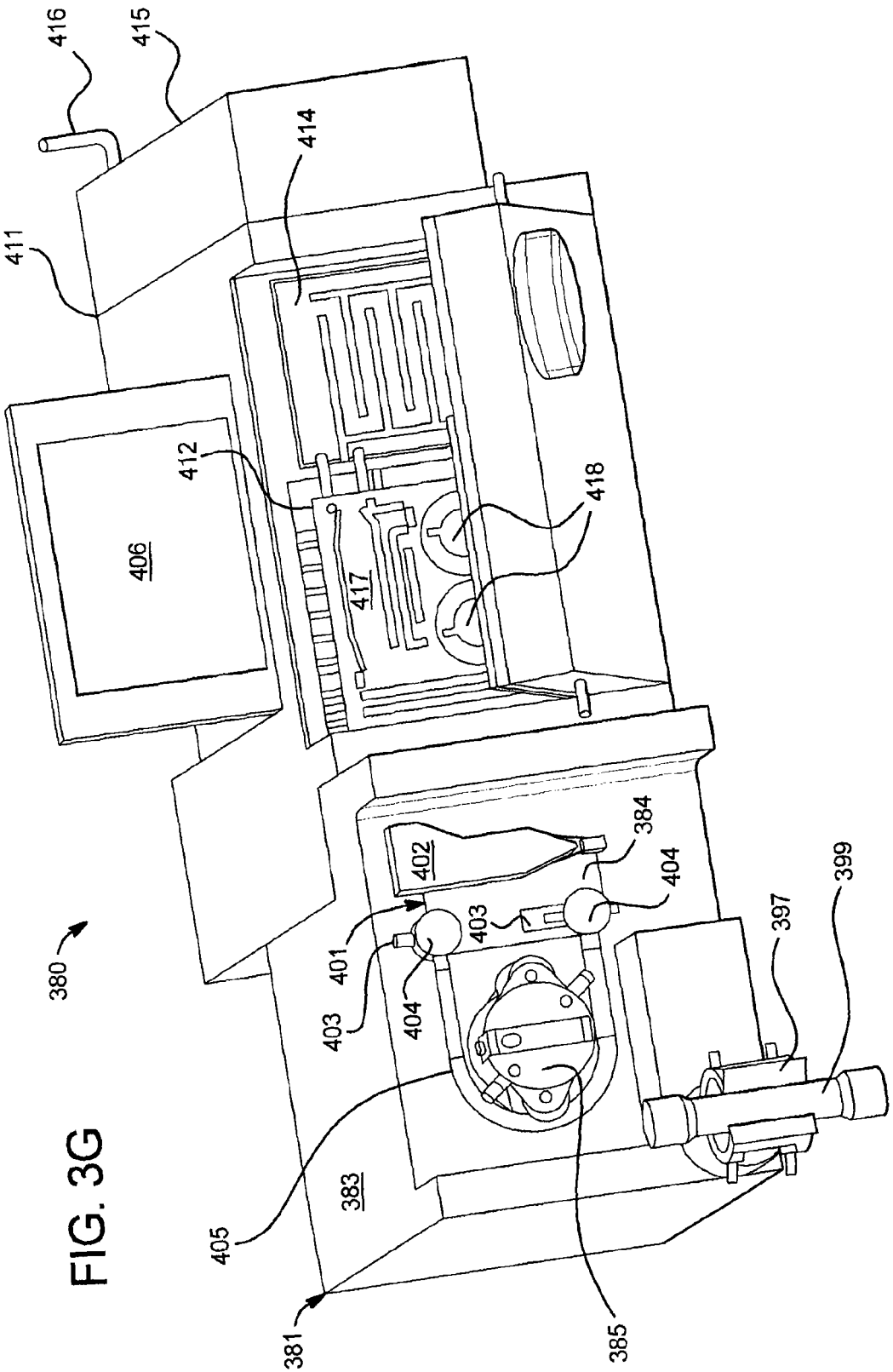

FIG. 3G depicts dialysis system 380 configured for a blood treatment or hemodialysis use and includes many apparatuses also used for peritoneal dialysis, including an ozone generator so that the cassette may be reused. These include a hemodialysis unit 381, a dialysate unit 411, a viewing screen with a graphical user interface 406, a cassette interface (not shown) and cassette 412. Hemodialysis unit 381 can be operated externally from dialysate unit 411, e.g., via wired or wireless communication, or be physically and electronically docked to dialysate unit 411. The hemodialysis portion 381 includes blood pump 385, and dialyzer holder 397 for dialyzer 399. Dialyzer holder 397 clamps onto and holds dialyzer 399 when system 380 is to be used for a blood treatment, such as hemodialysis. Dialysis system 380 also includes an ozone generator 415, as described above, and an inlet connection 416 for sterile water, preferably a container of sterile water. FIG. 3G also shows hemodialysis or blood treatment cassette 401 installed, such that pump tubing 405 of cassette 401 is pulled around and placed in operable communication with blood pump 385.

Hemodialysis disposable dialysate cassette 412 includes an attached fluid heating pathway 414 as discussed above, which attaches to a valve and pump portion 417 of cassette 412. Valve and pump portion 417 includes ports, flow paths and valve port seats as are well known in the dialysis arts. Hemodialysis dialysate cassette 412 defines or includes multiple pumping portions 418. Blood cassette 401 includes peristaltic pumping tube 405. Peristaltic pumping tube 405 connects fluidly to a sensor portion 384, which can be made of any one or more of the rigid or sheeting materials, such as PVC, non-DEHP PVC, norprene, silicone, pharmel, pharmapure, C-flex, Viton, polybutadiene ("PB"), ethylene vinyl acetate ("EVA"), polypropylene ("PP") blend, polyethylene ("PE") blend, Kraton® blend and polyolefin blends. Sensor portion 384 includes a blood and air separation receptacle 402 and a pair of pressure sensor interfaces 404 and 406. Pressure sensor interfaces 404 enable arterial and venous pressures to be measured. Priming and rinseback connections 403 connect fluidly to pressure sensor interfaces 404 as illustrated. It is understood that in hemodialysis, the dialysate fluid flows to the dialyzer, not directly to the patient, and therefore the cassette for a hemodialysis machine does hot have a "patient output line," but rather an output to the dialyzer, and a recirculation line from the dialyzer. The ozonated solution may also be circulated through the dialysate side of the dialyzer, or the input/output lines may be connected directly. With proper procedures, and after priming with sterile water or dialysate, the blood side of the dialyzer may also be cleansed with ozonated water.

It is believed that treating sterile water or other disinfecting fluid with ozone will allow reuse of the dialysis cassette, if the ozone is generated in bio-available quantities of at least about 0.3 to about 0.6 ppm (mg/L). In testing to date, concentrations of about 2-4 ppm ozone were effective in eliminating microorganisms from a dialysis disposable cassette set, including the cassette, lines to and from the patient, and the drain line. As shown in FIG. 3F, the disposable 25 is arranged such that sterile water will receive ozone from ozone cell 368. The ozonated water will then enter input line 20. The remaining input lines may be end-capped 371 so that the ozonated water will circulate among the other input lines 54, through the cassette 25 and its internal plumbing, and then out through the patient out line 361, and back in through end cap 365 to the patient in line 363. Finally, the spent ozonated water will be sent to the drain line 32. It is estimated that about 5-10 minutes of circulation of the ozonated water at the above concentration will be sufficient to kill at least 99.99% (a log 4 reduction) or more of the microorganisms present. These microorganisms include bacteria, viruses, fungi and yeast, and protozoan cysts. In addition to the 5-10 minutes of treatment, it may take an additional 5-10 minutes to make the proper fluid connections, turn on the ozonator cell, and warm the cell to its operating condition. Of interest to dialysis is *Serratia marcescens, S. aureus, P. aeruginosa*, and *E. coli*. Test results for *S. marcescens* to date have shown that circulating 2-4 ppm ozonated water was completely cidal.

In another way of ozonating the wetted portions of the disposable, a small supply of water (100-500 ml) may be placed in the ozonation cell, which is then started, and the ozonation concentration is brought to a high level, e.g. 1-5 ppm. A first cycle of flushing is begun using this water. This portion may be repeated several times to insure all dialysate is flushed from the cassette. The ozone generator is then set for lower ozone concentrations, about 0.5 to 1.0 ppm, and ozonated water is circulated for a length of time sufficient to achieve the desired reduction in the pertinent microorganisms. After this length of time, or testing, has shown the ozonation cycle to be complete, the cassette and all the lines may be flushed or rinsed with fresh sterile water. Alternatively, a length of time, 5-10 minutes may be used instead to let the remaining ozone in the water react.

A heated rinse cycle, with water temperatures form 40 C to 50° C., may be used to disinfect the disposable. The temperature of the water is preferably hot, but not so hot as to cause warping or other dimensional instability of the cassette, the connections, the dialysis machine or the dialysis machine controller. The higher temperature makes it easier for the water and dissolved water to vaporize, allowing the sanitizing ozone to more easily reach all the hard-to-reach corners and crevices of the dialysis machine. This very thorough coverage is believed to be necessary to a complete and thorough cleaning and disinfecting of the machine. Temperatures higher than 50° C. may of course be used, but it is believed that this is a good maximum temperature, considering the nature of some of the plastic materials typically used for peritoneal dialysis and hemodialysis cassettes, such as PE, PP, PVC, polysulfone, acrylic, COCs, and the like.

Another way to effectively spread the ozone-containing water throughout the cassette is to vaporize the water. Dialysis machines typically include a high pressure (about 7-10 psig) air tank 25c and a "negative" pressure air tank 25d containing air at about 7-10 psi below atmospheric (about 5-8 psia). This access to low pressure or partial vacuum may be used, in conjunction with heating, to vaporize the ozone-containing water and thus achieve more thorough ozone cleaning and decontamination in spots or areas that are hard to clean, e.g., corners in the cassette, bends in the tubing, crevices and cracks in the connectors, and so forth. It is believed that this vapor-cleaning by ozone-containing hot water, up to 40-50° C., helps to cleanse and decontaminate the cassette, lines, and connectors, making them suitable for subsequent dialysis treatment.

The techniques described above may be used in many different ways. For example, in one method, pre-chilled bags of low-conductivity deionized water may be connected via an input line and water from the bags allowed to flow to the electrolytic ozone cell. The ozone cell is then operated and water with concentrations of 4-6 ppm ozone are produced and pumped throughout the cassette, its connecting lines, the end-capped lines to and from the patient, and the drain line. This initial treatment, for about 10-15 minutes, will clearly rid the cassette of the bulk of any contamination present. Afterwards, the chill coils may be turned off, and the ozonated water heated from about 40-50° C. for circulation. At some point, the cassette may then be subjected to partial vacuum, using the "negative" pressure air tank. The lower pressure will help to vaporize at least a part of the heated, ozonated water, thus flashing an amount of the ozone into the areas for decontamination and cleansing. As the heated vapor contacts the walls of the cassette and lines, it reacts with undesirable microorganisms and helps to clean the cassette or other portions that are desired for reuse. Afterwards, the vapor condenses and is pumped out of the area.

In addition to using high and low temperatures, as discussed above, the operator may use high and low pressures to help achieve disinfecting. As noted, low pressure may be used to vaporize ozonated water, thus reaching into tiny corners or nicks that could otherwise harbor contaminants or microorganisms. After a low pressure cycle, high pressure air from the high pressure tank 25c may be used to force gas or liquid or both into areas of the disposable, and then pumped out. This pressure cycling may be used as often as desired as one way to disinfect the cassette and lines.

Afterwards, a normal procedure for the extended use cycle will include disconnecting the ozone generator from the cassette, as well as the ozone recirculation ports. The ports should be protected from contamination. Any end caps used are removed and protected, and the dialysis solution containers are then connected to the disposable for the next dialysis treatment. The patient input and output lines are connected to the patient, and the normal starting procedure for the dialysis machine and cassette are followed.

Inductive Heaters

Referring now to FIGS. 5A/5B to 13, various embodiments for inductive, inline dialysate heaters are illustrated. FIGS. 5A and 5B illustrate a first embodiment via heater 480. Heater 480 in one embodiment is operable with a disposable cassette, such as cassette 50 described for use with system 10 (e.g., FIG. 1A). Heater 480 in an embodiment is located externally with respect to cassette 50. Alternatively, heater 480 is incorporated directly into cassette 50. In either case, it is contemplated to place heater 480 upstream of the pump in one embodiment to help reduce the need to compensate for fluid temperature when determining pumping accuracy.

Heater 480 in the illustrated embodiment is a relatively small, multi-pass, disposable, inductive heater configured to heat dialysate, for example, from about 5 C to about 37 C (body temperature) at a dialysate flowrate of about 200 ml/min. Heater 480 includes a housing 482, such as a plastic or otherwise electrically insulative housing. Suitable materials for housing 482 include plastics approved for carrying injectable fluids. Housing 482 has a top wall 484, sidewalls 486 and 488, a bottom wall 490 and front and back walls (not seen). In the illustrated embodiment, heater 480 defines or includes a fluid inlet 492 and a fluid outlet 494. Metal or conductive plates or baffles 496a to 496d are located within the housing. The plates 496 (referring collectively to plates 496a to 496d) define a tortuous path for the dialysate to flow from inlet 492 to outlet 494. The illustrated embodiment shows four plates, but more or fewer plates may be used as desired. Plates 496 may have flow restricting baffles.

In one implementation the plates are heated to 47° C. to achieve the above-described desired fluid heating. Changing the number of plates 496 or total surface area of same would raise or lower the necessary plate temperature. The illustrated housing 482 is generally rectangular but could have a different shape. The aspect ratio or length l versus depth d of plates 496 can be varied as needed. As mentioned above, housing 482 may be incorporated into a disposable cassette (e.g., cassette 50) or operate upstream or downstream from the cassette. Plates 496 can be made from any of a variety of medically suitable metals, e.g., stainless steel, as desired to enhance the inductive heating of the plates. Plates 496 are covered with a protective plastic film in one embodiment allowing for better conducting metals to be used to form plates 496.

Plates 496 form a secondary coil of a transformer shown in more detail below in connection with electrical system 540 of FIG. 13. The primary coil of the transformer can be integral to dialysis machine 60 (e.g., FIG. 2C) and reusable. Dialysis machine 60 is configured such that the inductive heater portion of the disposable cassette is positioned onto or adjacent to the primary coil located within the dialysis machine. When energized, the primary coil induces a current into the shorted secondary coil (e.g., plates 496), heating the secondary, which in turn heats the inline flowing fluid. The primary and secondary coils are provided alternatively independently of the disposable cassette. Here, heater 480 is inserted independently onto the primary coil of the transformer, which can still be located within the dialysis machine. Still further alternatively, the primary coil of the transformer is located external to the dialysis machine.

One set of suitable dimensions for induction inline heater 480 is as follows. The dimensions are provided for illustration purposes only and are not intended to limit the scope of the disclosure in any way. The dimensions do demonstrate however that the inductive heater can be relatively small and is well-suited for incorporation into a disposable cassette. Again, the dimensions are sized in one embodiment to provide a heater 480 with the capacity to bring dialysate stored at about 5° C. to a therapy temperature of about 37° C., assuming a flowrate of about 200 ml/min. along a fluid pathway 498. To accomplish this requirement for the below-described dimensions, it is estimated that the temperature of plates 496a to 496d will need to be heated to about 47° C.

In the illustrated example, the length l and depth d of top 484 and bottom 490 of heater 480 is about 3.08 inches (7.82 cm) by 0.630 inches (1.60 cm), respectively. The height h of sidewalls 486 and 488 (and the front and back walls, not illustrated) is about 0.440 inch (1.12 cm). The thickness, $t_1$, of top wall 484, sidewalls 486 and 488 and bottom wall 490 is about 0.065 inch (0.17 cm). The thickness of the non-illustrated front and back walls in an embodiment is the same as thickness $t_1$.

The thickness $t_2$ of heating plates 496a to 496d in one embodiment is about 0.04 inch (1.02 mm). Plates 496 as mentioned above are made in one embodiment of stainless steel, such as stainless steel 304 or 316. Plates 496 can be made of other suitable, non-corrosive, medically compatible, inductively heatable material, such as stainless steel 304, 316 or 430. The plates used for the above-described dimensions 1, h and d for housing 482 are about 2.85 inches (7.24 cm) long by 0.500 inches (1.3 cm) deep in one embodiment. Plates 496a to 496d can be spaced apart from each other and from top wall 454 and bottom wall 490 a gap distance g of about 0.03 inches (0.08 cm). The spaces s left between the ends of plates 496a to 496d and the inner surfaces of sidewalls 486 and 488 are 0.100 inch (0.25 cm) in one embodiment. While gaps g, thicknesses $t_1$ and $t_2$, and spaces s are each described as being the same or constant, it is contemplated to vary one or more of those dimensions as needed. It is also expressly contemplated to provide a filter or a trap, or both, to remove any particles from the dialysate before the dialysate enters heater 480 to preserve the free flow of fluid through relatively narrow pathway 498.

The dimensions of inlet 492 and outlet 494 can be for example 0.250 inch (6.35 mm) inner diameter and 0.275 inches (6.99 mm) long, with a wall thickness of 0.065 inch (1.65 mm). Inlet 492 and outlet 494 can have flanged or integral ferrule-type apparatus to connect sealingly to heater lines 68 for example or with internal tubes disposed within disposable cassette 50. Inlet 492 and outlet 494 are formed alternatively integrally with one or more passages of cassette 50.

In the illustrated embodiment, inlet 492 is located elevationally above outlet 494. This is advantageous in one respect because air or gas coming out of solution while being heated along pathway 498 tends to rise toward the top of heater 480 along gaps g, leaving at least substantially pure heated fluid or dialysate flow from the bottom of heater 480 through outlet 494. In an alternative embodiment, heater 480 is rotated ninety degrees from the orientation shown in FIGS. 5A and 5B, so that plates 496 are disposed vertically. Inlet 492 can be horizontally disposed. Outlet 494 can be horizontally disposed or disposed downwardly and in communication with pathway 498 between plate 496d and wall 490. Gas digression from solution flowing along vertical plates 496 rises to the top of heater 480, causing at least substantially air-free dialysate to leave outlet 494.

Inline heater 480 eliminates the need for warmer bags 350 and 400 described above. In any of the orientations discussed above, inline heater 480 can include a separate air separation chamber or other air/gas purge apparatus, for example, as part of cassette 50 (e.g., FIG. 2C). Heater 480 can also be provided with a hydrophobic membrane or a separator post having same for air/gas purging purposes.

Figure 6:
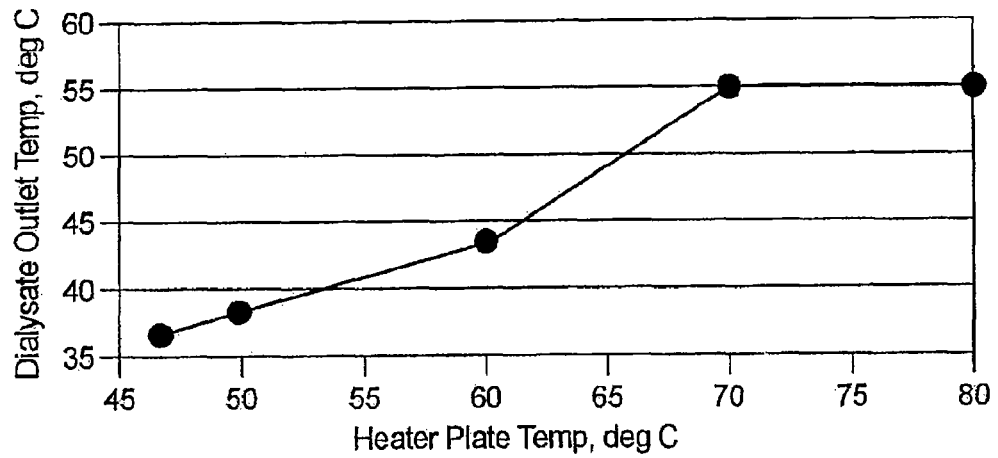
FIGS. 6 to 8 are charts showing various performance characteristics of the inductive fluid heater of FIGS. 4 and 5.
Figure 7:
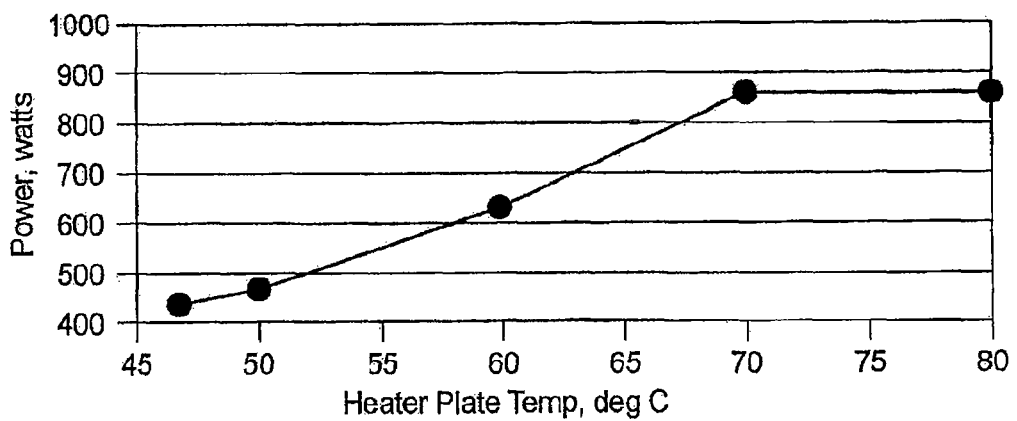
Figure 8:
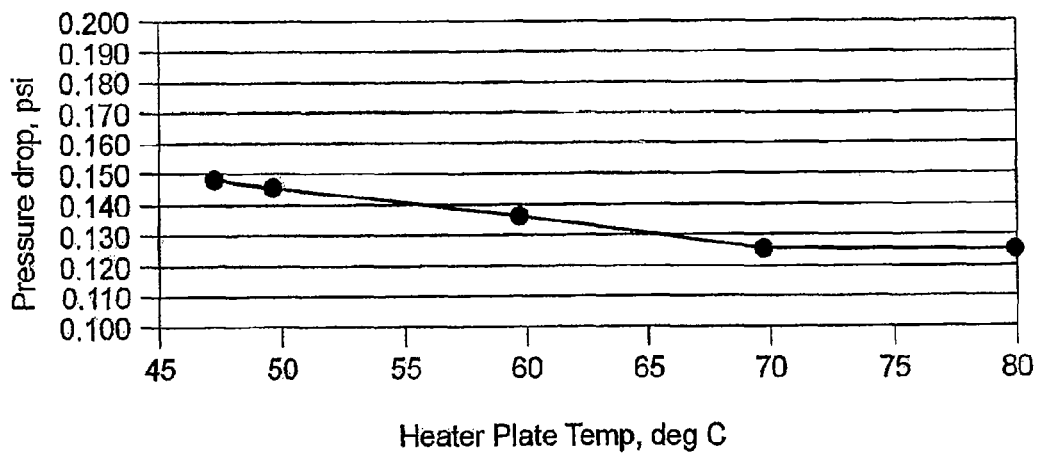

Referring now to FIGS. 6 to 8, various performances curves or charts for inline, inductive heater 480 are illustrated. The charts again apply to dialysate flowing at a rate of about 200 ml/min, which is being from about 5° C. to a desired temperature of about 37° C. FIG. 6 illustrates that heating plates 496a to 496d to a temperature of about 47° C. will heat the dialysate to about 37° C. or above. Heating plates 496 to about 70° C. will increase the outlet dialysate temperature to about 55° C.

FIG. 7 illustrates that heating plates 496a to 496d to a temperature of about 47° C. requires about 430 to about 440 Watts of power. Heating the plates to a temperature of about 70° C. requires about 880 to about 890 Watts of power.

FIG. 8 relates heater plate temperature to dialysate pressure drop occurring along heating pathway 498. As plate temperature increases, the corresponding pressure drop decreases. Heating plates 496a to 496d to a temperature of about 47° C. causes a corresponding pressure drop of about 0.15 psig. This pressure drop is manageable given the operating pressure of the medical fluid pump of system 10, which can be about two to three psig.

As mentioned above, heater 480 can be modified to have more or fewer plates 496 which are heated to lower or higher temperatures, respectively. Plates 496 can be varied to have different aspect ratios (length l to depth d ratio). Plates 496 may be smooth or textured. Heater 480 can also be configured such that plates 496 contact the fluid or dialysate directly or are alternatively provided with a film, such as a plastic film. Further alternatively, secondary coil plates 496 may be incorporated into unit 60 of system 10 (e.g., FIG. 1A), reducing the cost of the disposable cassette 50 (e.g., FIG. 2C). Here, pathway 498 can serpentine back and forth within a disposable pathway, which is positioned along one or more plates 496 located within unit 60. For example, unit 60 can have a clamshell shape, wherein plates 496 are disposed on opposing inner surfaces of the clamshell. The disposable pathway is placed between and in contact with the disposable pathway. Here, plates 496 can be of a material optimized for heat transfer since the plates do not contact the fluid directly.

Figure 9:
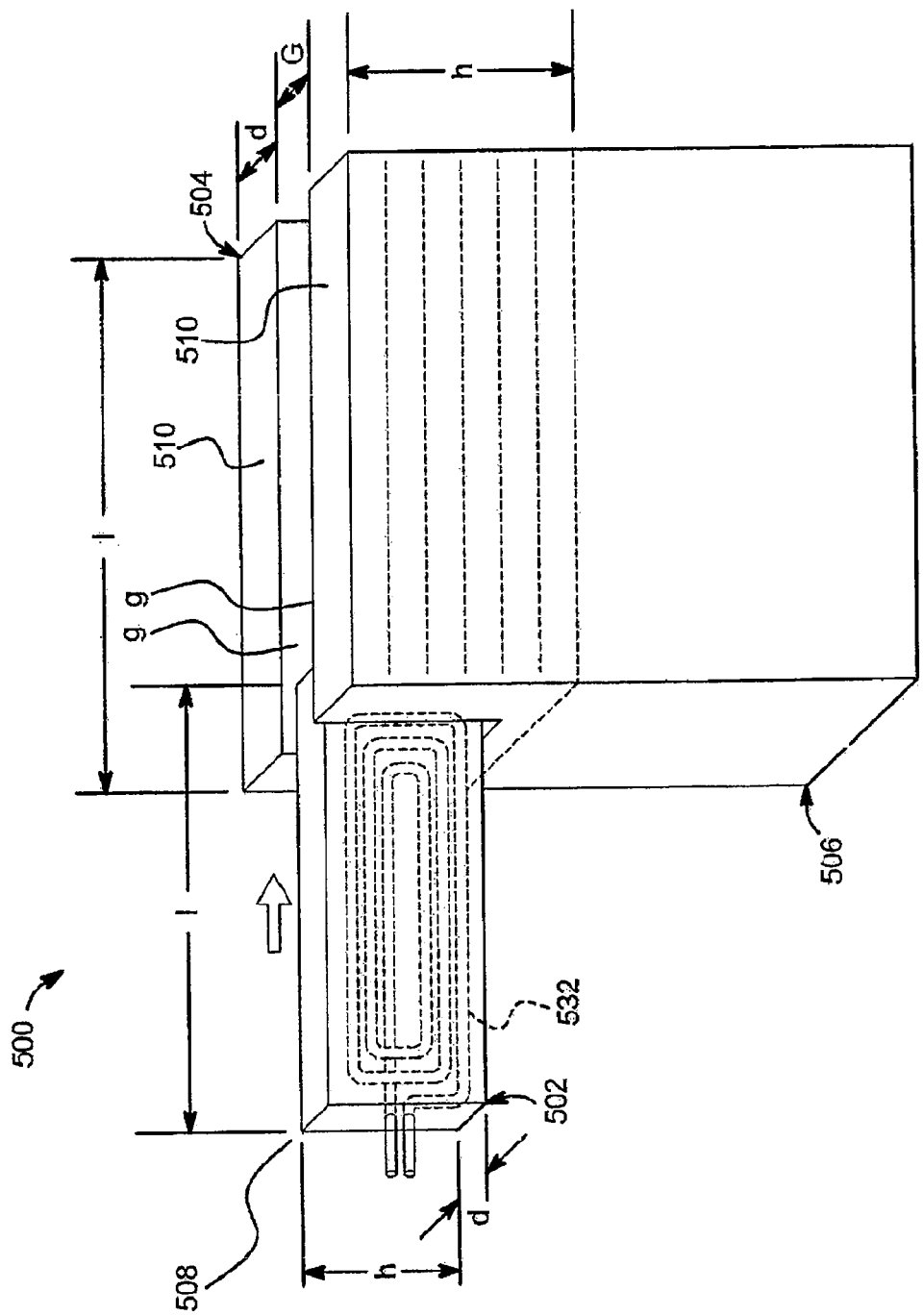
FIG. 9 is a perspective view of a second embodiment of an inductive disposable-cassette mountable dialysis fluid heater.
Figure 10:
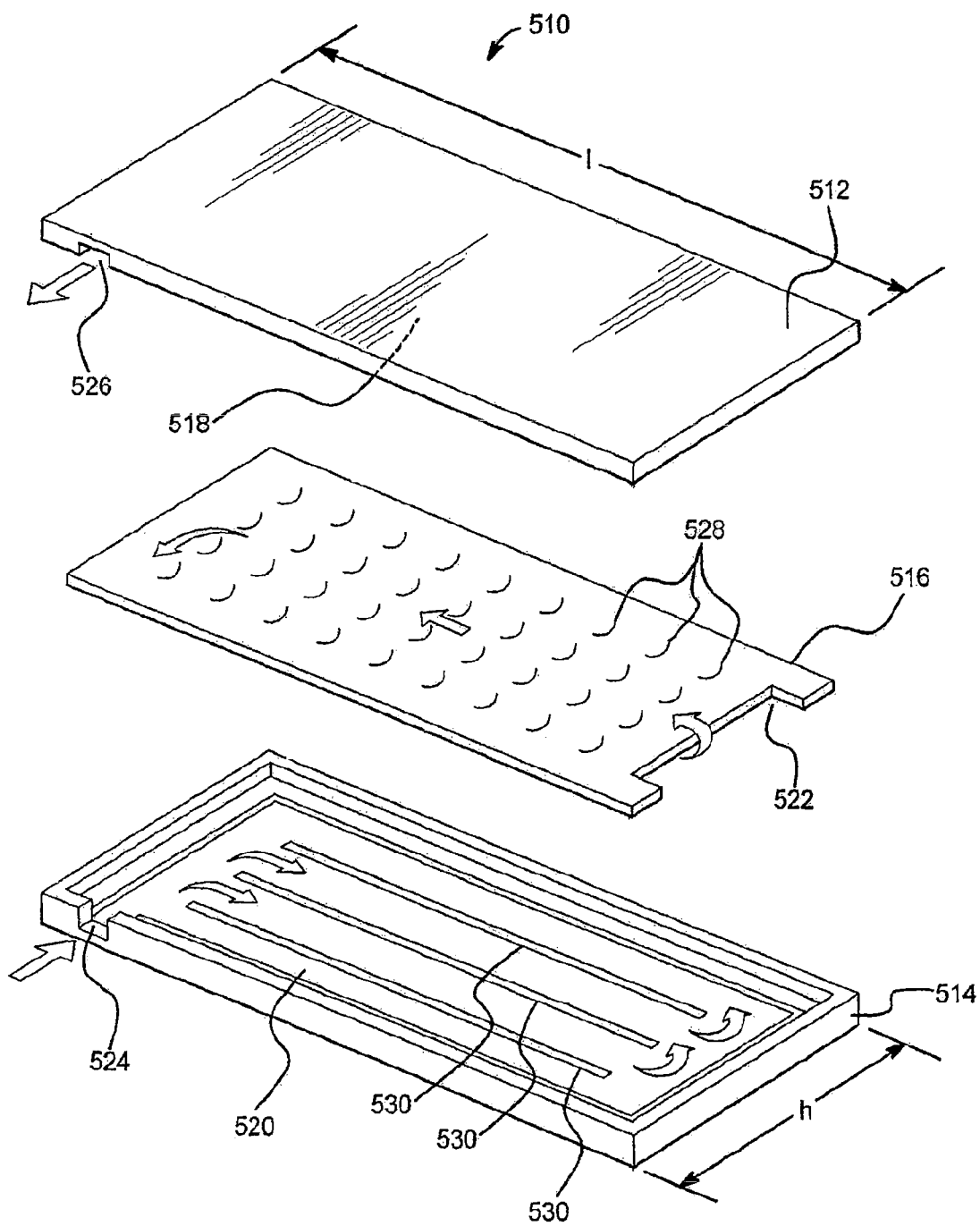
FIG. 10 is a perspective view of the heater of FIG. 9 incorporated into a disposable-cassette.

Referring now to FIGS. 9 and 10, an alternative embodiment of an inductive, inline fluid heater is illustrated by heater 500. The primary components of heater 500 include an induction coil block 502, which fits inside of or adjacent to a disposable fluid heat channel 504. In the illustrated embodiment, fluid heating channel 504 is U-shaped and fits around the sides of induction coil block 502. Alternatively, heating channel 504 is exposed to only a single surface of induction coil block 502.

Induction coil block 502 in one embodiment is provided as part of the hardware unit 60 of system 10 (e.g., FIG. 2A). Fluid heating channel 504 in one embodiment is formed integrally with (and is, e.g., upstream of) cassette area 506 of the disposable cassette, which is dedicated to pumping and valving. Locating fluid heating channel 504 of the cassette upstream of the pumping and valving portion 506 of the disposable cassette helps to reduce the amount of temperature compensation needed for pumping accuracy.

As discussed above with heater 480, the inline nature of heaters 480 and 500 eliminates the need for a batch warmer bag. The relatively rigid inductive heating systems 480 and 500 can be less "floppy" than batch heating systems and thereby easier to load. System 500 is constructed so that fluid heating channel 504 is readily aligned and made operable with induction coil block 502.

One set of suitable dimensions for heater 500 is set forth below. The dimensions serve as an illustrative example and in no way are meant to limit the scope of the disclosure. Block 502 includes an e.g., plastic housing 508, which in an embodiment is shaped as a flat plate having overall dimensions l×h×d of about 2 inches×2 inches×0.125 inch thick (5.08 cm×5.08 cm×3.18 mm) or 1 inch×4 inches×0.125 inch thick (2.54 cm×10.2 cm×3.18 mm). Housing 508 holds coil 532. Coil 532 can be any suitable metal because it does not contact the dialysate directly, such as, steel or stainless steel. Coil 532 in one preferred embodiment is Litz Wire. Coil 532 in one embodiment is a three inch diameter pancake type coil.

Fluid heating channel 504 includes a pair of sub-channels 510, which form the sides of the U-shaped channel 504. Each sub-channel 510 of U-shaped channel 504 in one embodiment has overall dimensions l×h×d of about 2.5 inches×2.5 inches×0.25 inch thick (6.35 cm×6.35 cm×6.35 mm) or about 1.5 inches×4.5 inches×0.25 inch thick (3.81 cm×11.4 cm×6.35 mm). The sub-channels 510 define a gap G between the sub-channels. In one implementation, the clearance or little gap g between each of the outer surfaces of induction coil block 502 and the opposing inner surfaces of sub-channels 510 of fluid heating channel 504 is just enough to allow induction coil block 502 to fit within gap G.

Referring now to FIG. 10, one of the sub-channels 510 is shown exploded. Each sub-channel 510 includes a first cover portion 512 and a second cover portion 514, which surrounds a heater plate 516. Heater plate 516 is sized to create first and second fluid flow plenums 518 and 520, between the top surface of plate 516 and the bottom surface of first cover portion 512 and the bottom surface of plate 516 and the top surface second cover portion 514, respectively. Covers 512 and 514 are plastic in one embodiment and are sealed together via any of the methods described herein. Plenums 518 and 520 can each have a volume defined by the dimensions for sub-channels 510 set forth above.

Plate 516 is sized to fit within the walls of covers 512 and 514. Plate 516 defines a notch 522 that allows fluid or dialysate to flow from second plenum 520 to first plenum 518, respectively, as indicated by the arrows shown in FIG. 10. Lower cover portion defines a fluid inlet 524, which receives fluid from: (i) a supply bag 14, 16 or 22; (ii) cassette portion 506; or (iii) the other sub-channel 510 depending upon whether the illustrated sub-channel 510 is upstream or downstream of the other sub-channel 510. Likewise, upper cover portion 512 defines an outlet 526, through which dialysate exits sub-channel 510 to: (i) cassette portion 506; (ii) the patient; or (iii) the other non-illustrated sub-channel 510.

Heating plate 516 can be any suitable medically compatible and inductively heatable material such as stainless steel. As illustrated, plate 516 can have perforations, ribs, baffles or other flow obstructions 528, which: (i) increase surface area contact with the dialysate; (ii) increase contact time; (iii) provide turbulence to the fluid flow; and (iv) increase the efficiency of heater 500. First and second cover portions 512 and 514 can additionally or alternatively have internal ribs or baffling, such as ribs 530, which direct or provide turbulence to, or both, the flow of dialysate through plenums 518 and 520, respectively.

Figure 11:
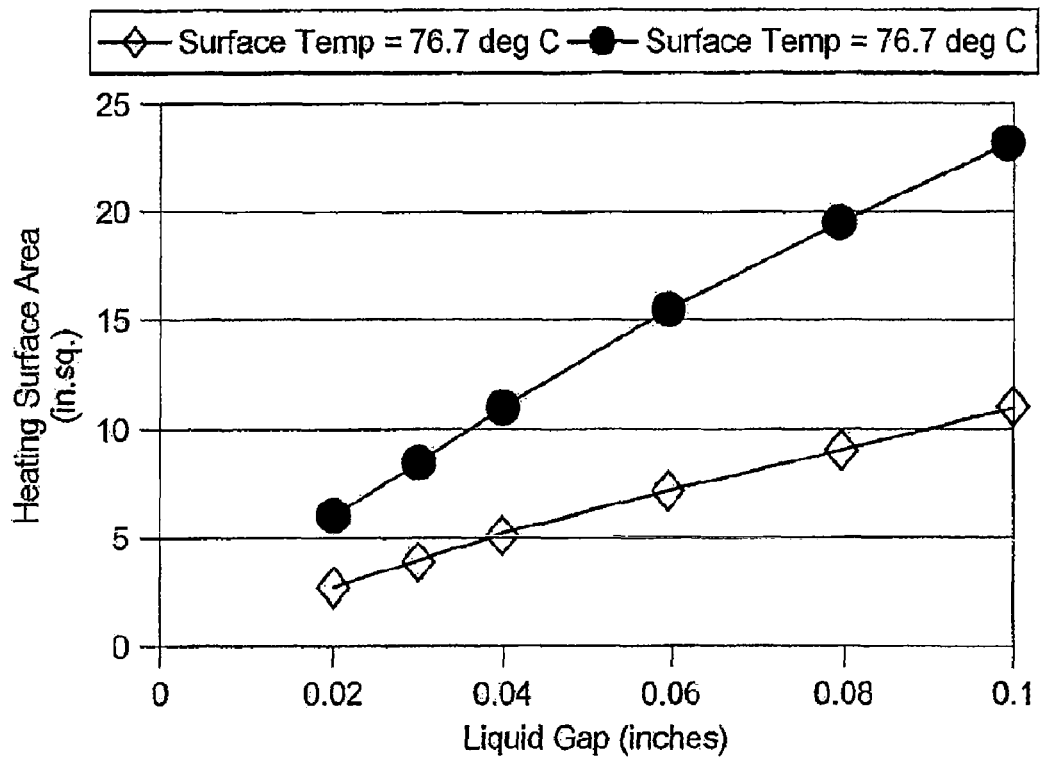
FIG. 11 is a chart relating heating surface area and liquid gap given a specified heating requirement for the heater of FIG. 9.

Referring now to FIG. 11, a chart is shown that relates the combined surface area of plates 516 of both sub-channels 510 required to heat dialysate from 5° C. to 37° C. at a flowrate of 200 mL/min as a function of gap for two different plate temperatures. The gap here is the distance between plate 516 and the inner surfaces of covers 512 and 514. As illustrated, the required combined surface area for a plate temperature of 76.7° C. (diamonds) ranges from about 2.5 in$^2$ (16.1 cm$^2$) to about 11 in$^2$ (71 cm$^2$) as the gap increases from about 0.03 inch (0.08 cm) to about 0.10 inch (0.25 cm). The required total surface area (circles) for a plate temperature of 47° C. ranges from about 6 in$^2$ (39 cm$^2$) to about 23.5 in$^2$ (152 cm$^2$) for the same gap range. The gap size is chosen to balance heating efficiency with providing enough space so that flow through heater 500 does not become obstructed. As with heater 480, suitable filtration may be placed upstream of heater 500 to remove at least most of the particles that could block the flow path(s) within heater 500.

Figure 12:
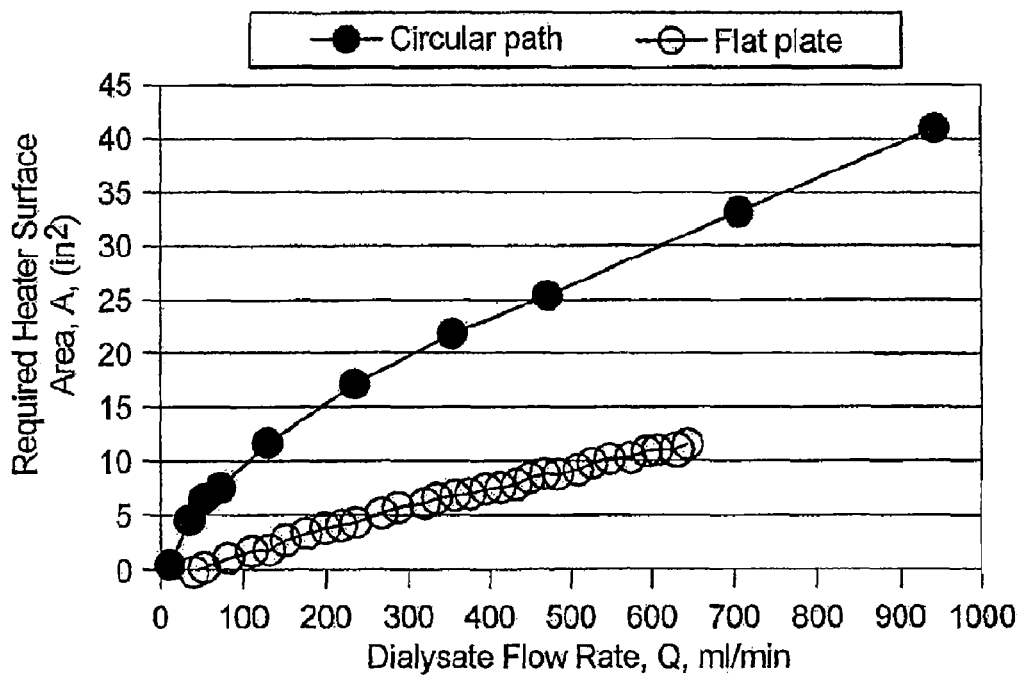
FIG. 12 is a chart relating heating surface area and dialysate flowrate for circular path versus flat plate inductive heaters.

FIG. 12 is a chart relating required heating surface area for the temperature rise described above for the chart of FIG. 11. A gap of 0.04 inches (0.1 cm) and a surface temperature of 170° F. (77° C.) for two different inductive heaters, namely, a circular flow path (dark circles) heater and a flat plate heater (light circles), such as heater 500. One example of an inductive fluid heater having a circular flow path is described in commonly owned patent application Ser. No. 10/982,170, entitled "High Convection Home Hemodialysis/Hemofiltration and Sorbent System," filed Nov. 5, 2004, the entire contents of which are incorporated herein by reference.

Summarizing the disclosure of the referenced application briefly, the heater in that application is cylindrically shaped with inner and outer tubes cooperating with a cylindrical element to form the dialysate flow path. Cold fluid is pumped into the induction heater along the inside of the outer tube and the outside of the heater element, around the bottom of the element, then along the inside of the element and outside of the inner tube before finally exiting the heater from the top.

For the cylindrical inductive heater, initial calculations have been made, which indicate that a surface area of less than ten square inches is required to heat the fluid from 5° C. to 37° C. degrees at a dialysate flowrate of approximately 150 ml/min. Using both sides of the element, ten square inches equates to a heater element sized for example at approximately one inch (2.5 cm) in diameter by about 1.5 inches (3.8 cm) long. This results advantageously in a small fluid heater.

As seen in FIG. 12, the required surface area for a circular flow path heater (dark, filled-in circles) varies non-linearly to about 41 in$^2$ (265 cm$^2$) as flowrate increases to over 900 mL/min. The required surface area for the flat plate flow path (open circles) varies more linearly to about 12 in$^2$ (77 cm$^2$) as flowrate increases to over 600 mL/min. Flat plate heater 500 appears to be more efficient than the circular flow path heater incorporated above by reference.

Figure 13:
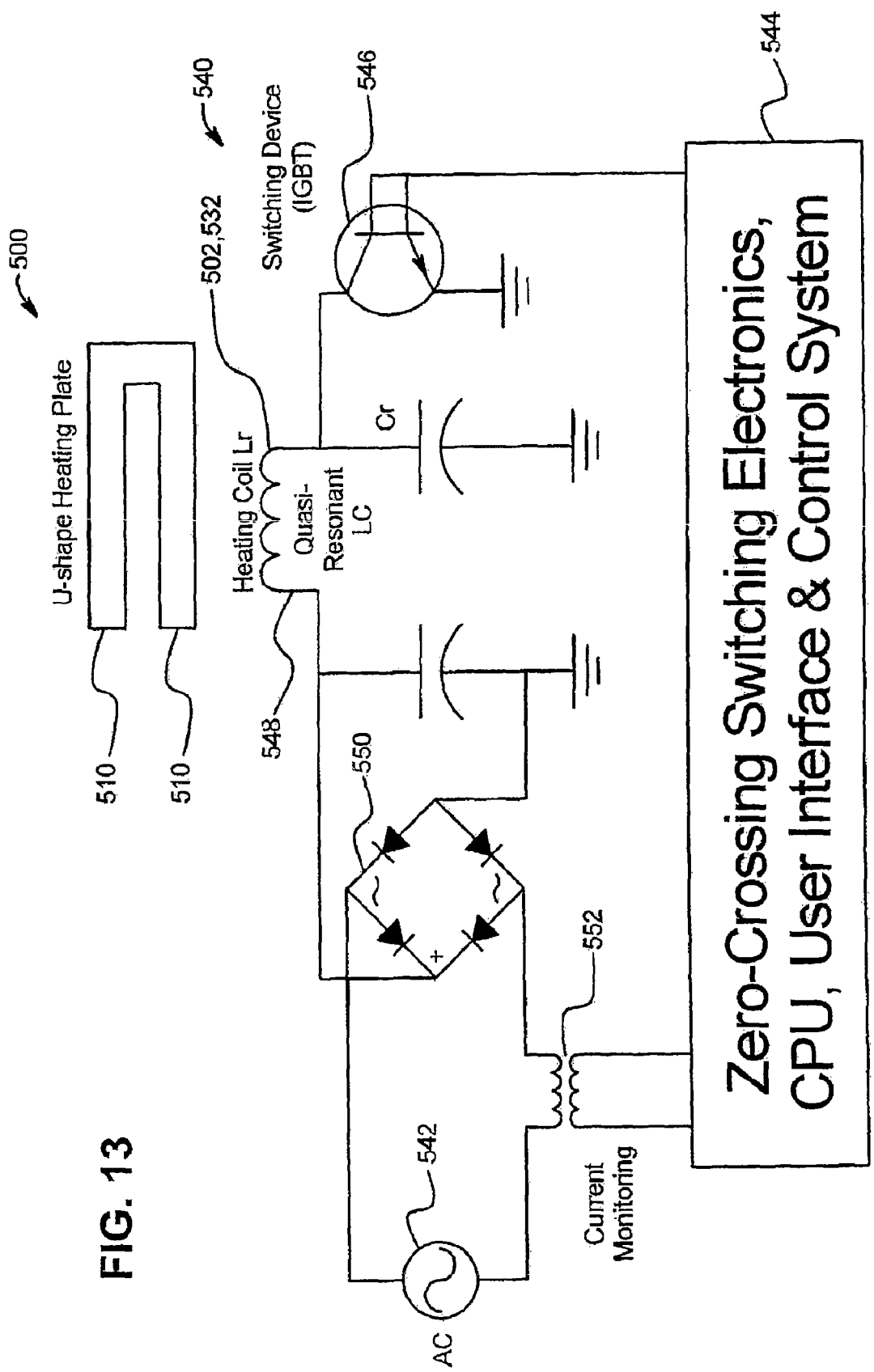
FIG. 13 is an electrical schematic for the inductive heaters of FIGS. 5A/5B and 9/10.

Referring now to FIG. 13, an electrical system 540 for both heaters 480, 500 is illustrated. Electrical system 540 includes an alternating current voltage source 542, which can be for example a 120 VAC or 240 VAC house or facility supply voltage. System 540 includes a control system 544, which can include a supervisory control processor, a delegate control processor or both. System 544 can also include one or more safety processor that monitors the operation of heater 480 or 500 to ensure its proper operation. At least one of the processors operates with a user interface, such as a display panel. The processor can control power to the primary coil based on feedback concerning any one or more of: (i) the temperature of the secondary coil, (ii) the temperature of the heated fluid, (iii) the initial temperature of the fluid, and (iv) the flowrate of the fluid. The feedback is provided by suitably placed temperature/flow sensors. The user interface allows the user to set dialysate temperature and dialysate flowrate for example. Control system 544 also houses zero-crossing switching electronics, which is well suited for high efficiency transistor switching.

The zero-crossing switching electronics operate an insulated gate bipolar transistor ("IGBT") type switching device 546. The IGBT device 546 in one embodiment is an IGBT 60 amp, 1 kV device, which has zero voltage across the associated transistor and zero current through the transistor. IGBT switching device 546 in turn controls a quasi-resonant LC circuit 548, which energizes the primary coil 532 of unit 502. A quasi-resonant LC circuit 548 is used in one embodiment. Coil 532 of unit 502 in can range from about 80 to about 170 μH in inductance. Coil 532 can be energized to ten amperes (wire capability) and have a pancake coil diameter of about three inches (7.6 cm). Circuit 548 can have a resonant frequency of about 30 kH to 50 kH. The power requirement from source 542 is for example from about 300 W to about 600 W.

A bridge rectifier 550 is connected between power source 542 and quasi-resonant LC circuit 548.

It should be understood that various changes and modifications to the presently preferred embodiments described herein will be apparent to those having skill in the art. Such changes and modifications can be made without departing from the spirit and scope of the present disclosure and without diminishing its intended advantages. Such changes and modifications are included in the appended claims.

What is claimed is:

1. A method for extending use of a disposable kit of a dialysis system, the method comprising:
   providing a disposable kit for use in a dialysis system;
   providing dialysis for a patient, by circulating dialysis solution through the disposable kit from at least one supply line for dialysate solution to a patient output line and back from the patient through a recirculation line, at least one of the lines running through the disposable kit;
   connecting the patient output line to the recirculation line;
   generating ozone to prepare a disinfecting solution;
   flushing the disinfecting solution through the patient output line and recirculation line;
   flushing the disinfecting solution through a pump and the at least one supply line for dialysate solution;
   draining the disinfecting solution from the disposable kit before a subsequent use of the disposable kit; and
   rinsing the disposable kit, including the at least one supply line, the pump, the patient output line and the recirculation line with sterile water before a subsequent use of the disposable kit, wherein one of the steps of flushing includes vaporizing a portion of the disinfecting solution.

2. The method of claim 1, further comprising heating the disinfecting solution to a temperature of at least 25 to 50° C.

3. The method of claim 1, wherein water used for the disinfecting solution is sterile water produced via distillation or reverse osmosis.

4. The method of claim 3, further comprising cooling the water used for the disinfecting solution to a temperature between 0 and 20° C. before or after the step of generating ozone and before the steps of flushing.

5. The method of claim 1, further comprising alternating between a high pressure and a low pressure within the disposable kit during the steps of flushing.

6. The method of claim 1, wherein the disinfecting solution is heated by an in-line heater to a temperature of at least 37° C. and optionally between 40 and 50° C.

7. The method of claim 1, further comprising preparing a disinfecting solution with ozone and flushing the disinfecting solution through the disposable kit before a first step of providing dialysis for the patient.

8. The method of claim 1, wherein water used for the disinfecting solution is sterile water with low conductivity.

9. The method of claim 1, further comprising recirculating the disinfecting solution through the disposable kit.

10. A method for extending use of a cassette for a dialysis system, the method comprising:
    providing a disposable kit for use in a dialysis system;
    connecting an output line of the kit to a recirculation line of the kit;
    generating ozone to prepare a disinfecting solution;
    flushing the disinfecting solution through a supply line into the kit;
    flushing the disinfecting solution through a pump, the output line, and the recirculation line, wherein the disinfecting solution is subjected to pressure cycles while being pumped, thus vaporizing at least a portion of the ozone in the disinfecting solution;
    draining the disinfecting solution from the disposable kit before a subsequent use of the disposable kit; and
    rinsing the disposable kit, including the supply line, the pump, the output line and the recirculation line before a subsequent use of the disposable kit.

11. The method of claim 10, further comprising heating the disinfecting solution to a temperature of at least 25° C.

12. The method of claim 10, further comprising cooling water used for the disinfecting solution to a temperature between 0 and 20° C. before or after the step of generating ozone.

13. The method of claim 10, wherein water used for the disinfecting solution has a conductivity of less than 50 microSiemens.

14. The method of claim 10, further comprising preparing a disinfecting solution with ozone and flushing the disinfecting solution through the disposable kit before a first step of providing dialysis for the patient.

* * * * *